(12) United States Patent
Mitarai et al.

(10) Patent No.: US 8,454,979 B2
(45) Date of Patent: Jun. 4, 2013

(54) IMMUNOPOTENTIATING COMPOSITION AND PROCESS FOR PRODUCING SAME

(75) Inventors: Kaoru Mitarai, Oita (JP); Yoji Nagahama, Tokyo (JP)

(73) Assignee: MEISHO Co., Ltd., Sakai-shi, Oita (JP)

( * ) Notice: Subject to any disclaimer, the term of this patent is extended or adjusted under 35 U.S.C. 154(b) by 0 days.

(21) Appl. No.: 13/202,484

(22) PCT Filed: Feb. 22, 2010

(86) PCT No.: PCT/JP2010/001120
§ 371 (c)(1),
(2), (4) Date: Oct. 19, 2011

(87) PCT Pub. No.: WO2010/095463
PCT Pub. Date: Aug. 26, 2010

(65) Prior Publication Data
US 2012/0039946 A1    Feb. 16, 2012

(30) Foreign Application Priority Data

Feb. 20, 2009   (JP) .................................. 2009-061956

(51) Int. Cl.
*A61K 35/74*   (2006.01)
*C12P 39/00*   (2006.01)

(52) U.S. Cl.
USPC .............................. 424/282.1; 435/4; 435/42

(58) Field of Classification Search
None
See application file for complete search history.

(56) References Cited

FOREIGN PATENT DOCUMENTS

| JO | 2007-506789 A | 3/2007 |
|----|---|---|
| JP | 05-279394 A | 10/1993 |
| JP | 2000-004830 A | 1/2000 |
| JP | 2003-071479 A | 3/2003 |
| JP | 2005-530716 A | 10/2005 |
| JP | 2006-514601 A2 | 5/2006 |
| JP | 2006-137703 A | 6/2006 |
| JP | 2006-265212 A | 10/2006 |
| JP | 2007-117083 A | 5/2007 |
| JP | 2008-31153 A | 2/2008 |
| WO | 03/082212 A2 | 10/2003 |
| WO | 03/103598 A | 12/2003 |
| WO | 2005/030196 A2 | 4/2005 |

OTHER PUBLICATIONS

Steven B. Mizel, Plague vaccine combined with immunostimulant under investigation for bioterrorism, Medical Tribune 2005 6.16.
Steven B. Mizel, Aaron H. Graff, Nammalwar Sriranganathan, Sean Ervin, Cynthia J. Lees, Mark O. Lively, Roy R. Hantgan, Michael J. Thomas, James Wood, and Brian Bell; Flagellin-F1-V Fusion Protein Is an Effective Plague Vaccine in Mice and Two Species of Nonhuman Primates, Clinical and Vaccine Immunology, Jan. 2009; 16 (1): 21-8 Epub Nov. 5, 2008.
Lai Wei, Arian Laurence, Kevin M. Elias, and John J. O'Shea, IL-21 Is Produced by Th17 Cells and Drives IL-17 Production in a STAT3-dependent Manner, The Journal of Biological Chemistry vol. 282, No. 48, pp. 34605-34610, Nov. 30, 2007.
Kenji Hakanishi, Tomohiro Yoshimoto, Hiroko Tsutsui, Haruki Okamura, Interleukin-18 regulates both TH1 and TH2 responses, Annual Review of Immunology, vol. 19: 423-474, Apr. 2001.
Igaku Shoin "Standard Immunology" pp. 209, 2009.
Nakanishi K., IL-18 and Super Th1 type Allergy inflammation, Hyogo Medical University, Dec. 24, 2008.
Harumichi Ishigame, Shigeru Kakuta, Takeshi Nagai, Motohiko Kadoki, Aya Nambu, Yutaka Komiyama,Noriyuki Fujikado, Yuko Tanahashi, AOI Akitsu, Hayato Kotaki, Katsuko Sudo, Susumu Nakae, Chihiro Sasakawa, Yoichiro Iwakura, Differential Roles of Interleukin-17A and -17F in Host Defense against Mucoepithelial Bacterial Infection and Allergic Responses, Immunity 30(1):108-119, Jan. 2009.
Li Yang, David E. Anderson, Clare Baecher-Allan, William D. Hastings, Estelle Bettelli, Mohamed Oukka, Vijay K. Kuchroo & David A. Hafler, IL-21 and TGF-βare required for differentiation of human TH17 cells, Nature Jul. 17, 2008 vol. 454 No. 7202/ pp. 350-352.
Takehiro Nishi, Maki Ideta, and Kenichi Arakawa, "Shikatsukashita Nyusankin oyobi Koubokinfunnmatu no Touyoniyoru Inu hifuen heno Tiryou Houhou", 27th Doubutsu Rinshou Igakukai 2006, p. 194-195.

*Primary Examiner* — Padma V Baskar
(74) *Attorney, Agent, or Firm* — Konomi Takeshita

(57) ABSTRACT

Disclosed is an immunopotentiating composition comprising an effective immunostimulating substance which can activate natural immunity and a subsequent immunity mediated by lymphocytes without causing any damage to cells. Specifically disclosed is an immunopotentiating composition which is characterized by comprising, as an active ingredient, an immunostimulating substance produced by decomposing at least one bacterium selected from an MRE symbiotic bacteria group consisting of *Bacillus* sp. (FERM BP-11209), *Lysinibacillus fusiformis* (FERM BP-11206), *Bacillus sonorensis*, *Lysinibacillus* sp. (FERM BP-11207) and *Comamonas* sp. (FERM BP-11208).

13 Claims, 4 Drawing Sheets

SEQUENCE LISTING

```
<160> NUMBER OF SEQ ID NOS: 5

<210> SEQ ID NO 1
<211> LENGTH: 538
<212> TYPE: DNA
<213> ORGANISM: Lysinbacillus fusiformis

<400> SEQUENCE: 1
tggagagttt gatcctggct caggacgaac gctggcggcg tgcctaatac atgcaagtcg      60
agcgaacaga gaaggagctt gctccttcga cgttagcggc ggacgggtga gtaacacgtg     120
ggcaacctac cctatagttt gggataactc cgggaaaccg gggctaatac cgaataaytt    180
gtttcacctc atggtgaaac actgaaagac ggtttcggct gtcgctatag gatgggcccg    240
cggcgcatta gctagttggt gaggtaacgg ctcaccaagg cgacgatgcg tagccgacct    300
```

```
gagagggtga tcggccacac tgggactgag acacggccca gactcctacg ggaggcagca    360
gtagggaatc ttccacaatg ggcgaaagcc tgatggagca acgccgcgtg agtgaagaag    420
gatttcggtt cgtaaaactc tgttgtaagg gaagaacaag tacagtagta actggctgta    480
ccttgacggt accttattag aaagccacgg ctaactacgt gccagcagcc gcggtaat      538

<210> SEQ ID NO 2
<211> LENGTH: 538
<212> TYPE: DNA
<213> ORGANISM: Lysinbacillus sp.

<400> SEQUENCE: 2
tggagagttt gatcctggct caggacgaac gctggcggcg tgcctaatac atgcaagtcg     60
agcgaacaga gaaggagctt gctcctttga cgttagcggc ggacgggtga gtaacacgtg    120
ggcaacctac cctatagttt gggataactc cgggaaaccg gggctaatac cgaataatyt    180
atttcayctc atggtgaaat actgaaagac ggtttcggct gtcgctatag gatgggcccg    240
cggcgcatta gctagttggt gaggtaaygg ctcaccaagg cgacgatgcg tagccgacct    300
gagagggtga tcggccacac tgggactgag acacggccca gactcctacg ggaggcagca    360
gtagggaatc ttccacaatg ggcgaaagcc tgatggagca acgccgcgtg agtgaagaag    420
gatttcggtt cgtaaaactc tgttgtaagg gaagaacaag tacagtagta actggctgta    480
ccttgacggt accttattag aaagccacgg ctaactacgt gccagcagcc gcggtaat      538

<210> SEQ ID NO 3
<211> LENGTH: 525
<212> TYPE: DNA
<213> ORGANISM: Comamonas denitrificans

<400> SEQUENCE: 3
tggagagttt gatcctggac tcagattgaa cgctggcggc atgccttaca catgcaagtc     60
gaacggtaac aggtctttcg ggatgctgac gagtggcgaa cgggtgagta atacatcgga    120
acgtgcctag tagtggggga taactactcg aaagagtggc taataccgca tgagatctat    180
ggatgaaagc aggggacctt cgggccttgt gctactagag cggccgatgg cagattaggt    240
agttggtggg ataaaagctt accaagccta cgatctgtag ctggtctgag aggacgatca    300
gccacactgg gactgagaca cggcccagac tcctacggga gcagcagtg gggaattttg      360 gacaatgggg gaaaccctga tccagcaatg ccgcgtgcag gatgaaggcc ttcgggttgt    420
aaactgcttt tgtacggaac gaaaagtctt gggttaatac cctgggatca tgacggtacc    480
gtaagaataa gcaccggcta actacgtgcc agcagccgcg gtaat                    525

<210> SEQ ID NO 4
<211> LENGTH: 538
<212> TYPE: DNA
<213> ORGANISM: Bacillus sonorensis

<400> SEQUENCE: 4
tggagagttt gatcctggct caggacgaac gctggcggcg tgcctaatac atgcaagtcg     60
agcgaaccga cgggagcttg ctcccttagg ttagcggcgg acgggtgagt aacacgtggg    120
taacctgcct gtaagactgg gataactccg gaaaccggg gctaataccg gatgcttgat    180
tgaaccgcat ggttcaatta taaaaggtgg cttttagcta ccacttacag atggacccgc    240
ggcgcattag ctagttggtg aggtaacggc tcaccaaggc gacgatgcgt agccgacctg    300
agagggtgat cggccacact gggactgaga cacggcccag actcctacgg gaggcagcag    360
```

```
-continued tagggaatct tccgcaatgg acgaaagtct gacggagcaa cgccgcgtga gtgatgaagg    420
ttttcggatc gtaaaactct gttgttaggg aagaacaagt accgttcgaa cagggcggtg    480
ccttgacggt acctaaccag aaagccacgg ctaactacgt gccagcagcc gcggtaat     538

<210> SEQ ID NO 5
<211> LENGTH: 539
<212> TYPE: DNA
<213> ORGANISM: Bacillus sp.

<400> SEQUENCE: 5
tggagagttt gatcctggct caggatgaac gctggcggcg tgcctaatac atgcaagtcg     60
agcgaatgga ttaagagctt gctcttatga agttagcggc ggacgggtga gtaacacgtg    120
ggtaacctgc ccataagact gggataactc cgggaaaccg gggctaatac cggataacat    180
tttgaacygc atggttcgaa attgaaaggc ggcttcggct gtcacttatg gatggacccg    240
cgtcgcatta gctagttggt gaggtaacgg ctcaccaagg caacgatgcg tagccgacct    300
gagagggtga tcggccacac tgggactgag acacggccca gactcctacg ggaggcagca    360
gtagggaatc ttccgcaatg gacgaaagtc tgacggagca acgccgcgtg agtgatgaag    420
gctttcgggt cgtaaaactc tgttgttagg gaagaacaag tgctagttga ataagctggc    480
accttgacgg tacctaacca gaaagccacg gctaactacg tgccagcagc cgcggtaat    539
```

IMMUNOPOTENTIATING COMPOSITION AND PROCESS FOR PRODUCING SAME

SEQUENCE LISTING

The sequence listing for this application has been submitted in accordance with 37 CFR §1.821 and 37 CFR §1.52(e) as a text file entitled "Y09S014PCTUSSequenceListing.txt" created on Oct. 17, 2011, 5 kb. Applicants hereby incorporate by reference the sequence listing provided in the text file as both the paper copy and the computer-readable form (CRF) of the sequence listing required by 37 CFR §1.821.

CROSS REFERENCE TO RELATED APPLICATIONS

This application claims priority under 35 U.S.C. 119 based upon Japanese Patent Application Serial No. 2009-061956, filed on Feb. 20, 2009. The entire disclosures of the aforesaid applications are incorporated herein by reference.

FIELD OF THE INVENTION

The present invention relates to a composition that stimulates innate immunity thereby enhancing the antibacterial, antiviral, anti-inflammatory, and anticancer effects and that also affects the lymphocyte immune system so as to suppress inflammation.

Specifically, the composition in accordance with the present invention stimulates innate immune receptors such as TLR, NLR, and RIG, followed by activating innate immune response cells including macrophages, natural killer cells, and, natural killer T cells, as well as activating the lymphocytic immunity interlocked with innate immunity such as Th17 and Th1, or Treg or the like. In addition, said composition induces activation of a series of immune processes for producing IL-21 that suppresses excessive immune responses, thereby enhancing anticancer, antibacterial, antiviral, and anti-inflammatory effects and mitigating autoimmunity due to a runaway of CTL.

BACKGROUND OF THE INVENTION

Recent years have seen the importance of the role of innate immunity grow, commensurate with the increase in various diseases associated with the diversification of lifestyles. A study by Steven B. Mizel in one of the U.S. NIH grants projects revealed that a plague bacillus (*Yersinia pestis*) vaccine fused to a flagellin, one of the innate immunity ligands, increases an adjuvant effect to the vaccine thereof to about 500,000 times. This result suggests a potential magnitude of innate immunity generating an expectation for adjuvant effects of innate immunity ligands (See Non-Patent References 1 and 2).

Innate immunity receptors or similar sensors thereof are widely present in animals, plants, and microorganisms. Specifically, for the vertebrate innate immune receptors, TLR (Toll-like-receptor), NLR (Nod-like-receptor), and RLR (RIG-like-receptor) are present in or out of the cells, whereby these detect foreign invaders such as bacteria and viruses by way of substances (ligands) formed by degradation of bacteria, viruses and the like and identify them by pattern recognition. Ligands are produced in multiples depending on the types of bacteria and viruses, generally, varying in substance and concentration that are generated, resulting in an identification and an innate immunity response, with a subtly different pattern recognition dictated by a combination of their ligand groups.

Innate immune response cells, such as epithelial cells in humans, have TLR TLR-1 & 2, TLR-6 & 2, TLR-4 & MD-2, and TLR-5 act on the cell membrane; and bacterial or viral nucleic acids (DNA and/or RNA) degradation fragments from degeneration by lysosomal enzymes in the endosome or phagocytic phagosome activate TLR-3, TLR-7, TLR-8, and TLR-9. At work in the cytoplasm are NLR receptors that sense low molecular degradation products of bacteria such as NOD1 NOD2, NALP3, and NAIP5, IPAF, and RIG; and MDA-5, and the like that sense viral low molecular degradation products and/or nucleic acids.

These receptors, sensors of innate immunity, release interleukins and/or type I interferons (IFN-$\alpha$ family, IFN-$\beta$ and IFN-$\lambda$) or substances analogous thereto, for various antibacterial effects according to the combination of patterns of sensed degradation products of the respective bacteria and/or viruses thereof, thereby causing the neighboring cells to sense them. Upon sensing these substances, the cells simultaneously release antibacterials such as defensin, cathelicidine, and dermicidin and/or a group of antiviral substances, as many as several hundred types, called the ISG, thereby defending a group of friendly cells from the foreign invaders. Herein, the fact that living organisms release a large number of antiviral substances in countering the rapidly changing viruses has turned out to be one of the reasons that require the composition of the instant invention.

The second role of the innate immune receptors is to activate phagocytes present in a multicellular organism with a gut. Phagocytes have developed as cells with a shared responsibility of the moving innate immunity, in which its role is played in humans by macrophages, neutrophils, or the like. Macrophages particularly play important roles as commanders of the innate immune system. When receptors, innate immunity sensors, are stimulated, macrophages, neutrophils, and their peers are activated, launching a framework to fight off invaders such as bacteria and viruses.

Vertebrates, except for lampreys and hagfish, have developed a lymphocytic immune system that identifies self from non-self, reinforcing the immune system. In particular, the mammalian lymphoid immune system has undergone a sophistication and enhancement on the basis of a complement system. On the other hand, this has resulted in patients suffering from allergic and autoimmune diseases.

In particular, in mammals, when the receptors of innate immune response cells such as macrophages, dendritic cells, Langerhans cells, and microglia sense the presence of a respective ligand (stimulus-specific), this leads to the secretion, in accordance with the resultant pattern recognition, of interleukins such as IL-12, IL-6, IL-4, and TGF-$\beta$ that prompt T cell differentiation; IL-1$\beta$ and IL-23; and IL-2 that activate the differentiated T cells; and IL-25, IL-27, and IL-6, that suppress the activities of the differentiated T cells.

These processes have IL-21 release from Th17 or natural killer T cells bringing to apoptosis, or suppressing, B cells and memory T cells that have antibodies that attack the self thereby preventing autoimmune diseases from developing.

It has been clarified by kinetic analyses of RNAs expressed from DNA by microarrays that various combinations of the innate immunity ligands, combinations of antigens and innate immunity ligands, and the like lead to variety of changes to the processes and differences in actions thereof. This is because technological advances in kinetic analyses of DNAs and RNAs have permitted capturing changes, in time sequence thereof, of the expression process of innate immunity and lymphocyte immune system (the so-called acquired immunity), the apoptosis pathway, inflammation controls (anti-bacterial, anti-cancer) pathway, switching to an antiviral pathway, inflammation and inflammation control processes, and the like.

Elucidation of such innate immunity receptors TLR, NLR, and RLR and of subsequent physiological processes thereof holds the potential to revolutionize medicine. It therefore provides hope for paving the way to an ultimate solution to such problems that conventional medicine finds difficult to treat, such as "various types of cancer afflictions and/or polyp formation in precancerous stages", "viral diseases such as HIV, HCV, HPV, and HHV, and new type influenza" and "antibiotics-resistant bacteria and bacteria latent in the body," "inflammatory diseases such as various allergic diseases", and "various autoimmune inflammatory diseases."

Against the background of such a flow of technology, A. "Effective combination of innate immunity ligands" and B "The combination of antigen vaccines and innate immunity ligands" have come to have an extremely important meaning.

Among those that have been popularized in the past for innate immune ligands are, for example, LPS, R-848, imidazoquinoline, and flagellin. LPS is a ligand that activates TLR4 and MD2; imidazoquinoline and its derivatives are ligands that activate TLR7; and flagellin is a ligand that activates TLR5.

Although both imidazoquinoline and R-848 exhibit the same TLR activity, they produce different IFN-α types such that imidazoquinoline is used as a therapeutic agent for HPV (papillomavirus) while R-848 is used for HHV (herpes virus). This shows that even those agents with the same acceptor activity may exhibit different effects due to different ligands.

In addition, MDP (muramyl dipeptide) and its derivatives are innate immunity ligands noted since about 1985, and they activate TLR-2. MDP-Lys, a derivative thereof, is a pharmaceutical agent as an adjuvant. This has recently received renewed attention for its activation of NLRs, but it is never used alone. It has been noted that a combination with other ligands such as LPS, Lipid A, or the like can elevate its ligand effect.

In addition, Patent Reference 1 has a finding that IL-10 is unexpectedly produced with a complex ligand made up of IL-12-producing bacteria and/or yeast with non-IL-12-producing bacteria and/or yeast.

Thus, complex ligands provide a synergistic effect absent in single ligands, in addition, permit the sites of action thereof to be diversified, thereby allowing the LPS (endotoxin) as a ligand to spread its risks, if it had any negative effect at all. A reason such as this has led to a strong need to develop a complexly-working ligand. In particular effects of such ligands have come to have an important significance after the discovery of flagellin's powerful adjuvant effects.

Modern health care is up against a wall. Antibiotics that have been relied upon are ineffective for viruses and face serious problems of generating resistant-bacteria. There is also the side effect of anaphylaxis. Hormones, such as steroids, and immunosuppressive drugs increase the risks of pathogenic and/or opportunistic bacterial infection through the weakening of the immunity, with their use failing to restore living organisms including the human life to normal. In addition, it has also been strongly pointed out that treatment with inhibitors also suffers from adverse effects by hindering the normal living organism's systems. A continued use of ineffective drugs is also escalating health care costs. Also from the standpoint of dismantling this wall, a safe and outstanding innate immunity-active ligand is being sought.

PRIOR ART REFERENCES

Patent References

Patent reference 1: Japanese Laid-Open Patent Publication No. 2008-31153.
Patent reference 2: Japanese Laid-Open Patent Publication No. 2006-265212.
Patent reference 3: Japanese PCT Translation Publication, No. 2007-506789.
Patent reference 4: Japanese PCT Translation Publication, No. 2006-514601.
Patent reference 5: Japanese PCT Translation Publication, No. 2005-530716.

Non-Patent References

Non-patent reference 1: Medical Tribune 2005 6.16
Non-patent reference 2: Clin. Vaccine Immunol 2009 January; 16 (1): 21-8 Epub 2008 Nov. 5
Non-patent reference 3: J Biol Chem, Vol 282, Issue 48, 34605-34610, Nov. 30, 2007
Non-patent reference 4: Nakanishi K et al: Interleukin-18 regulates Th1 and Th2 responses Annu Rev Immunol 119, 423-474, 2001
Non-patent reference 5: Igaku Shoin "Standard Immunology" pp 209-p 211
Non-patent reference 6: Nakanishi K "IL-18 and Super Th1 type Allergy inflammation, Hyogo Medical University"
Non-patent reference 7: Immunity 30(1):108-119, 2009
Non-patent reference 8: Nature Jul. 17, 2008 Vol 454 No 7202/pp 350-352

SUMMARY OF THE INVENTION

The present invention, made in view of these findings, is aimed at providing a cytotoxicity-free and effective composition (ligand or adjuvant). Specifically, it is directed to providing a very safe composition (ligand or adjuvant) having a non-inflammatory disorder-inducing antibacterial effect, antiviral effect, anticancer effect, and an inflammation suppression effect including the runaway-suppression of CTL.

In addition, the present invention is aimed at providing a low molecular composition (low molecular ligand) that is readily permeable through the cell membranes. The ease of cell membrane permeation means that it allows stimulating in a complex way the innate immune receptors present three-dimensionally in the endosomes on the cell surface and in the cell as well as the in the cytoplasm.

Similarly, the present invention is aimed at providing a composition that stimulates three-dimensionally the innate immune receptor (ligand). The realization of a three-dimensional composition (ligand) permits one to expect a synergistic effect thereof, thereby further increasing safety. In addition, by being low molecular it can also provide an immunoactivator that can also be readily absorbed through the intestine and skin. It is possible to realize a composition which cannot be attacked by antibodies because it is low molecular, making it also usable as an injectable agent.

Furthermore, the present invention is aimed at providing a composition that can be used as adjuvant.

Kaoru Mitarai, one of the inventors of the present invention, collected aerobic soil fungi samples in a forest on a mountain near the city of Saiki City, Oita Prefecture, Japan, and cultured them over many years to obtain a strongly characteristic, stable group of symbiotic bacteria, which with more intensive research and experiments, resulted in the completion of the present invention.

In addition, the present inventors administered a low molecular degradation product obtained by degradation of bacterial cells from said symbiotic bacterial group to HIV-infected patients, when it was observed their conditions considerably improved, The CD4, an indicator of AIDS affliction, considerably increased in as short a period as a month, and all subjects gained vitality, which led us to name said group of symbiotic bacteria a "MRE symbiotic bacteria group". This means that the degradation products of the MRE symbiotic bacterial group enhance the innate immunity in patients, whereby the disease can be treated. In other words, the present invention provides an innate immune enhancing composition capable of enhancing a subject's immunity, comprising the degradation product from the MRE symbiotic bacterial group.

Therefore, in accordance with a first main aspect of the present invention, is provided an immune enhancing composition that enhances a subject's innate immunity by stimulating his innate immunity, comprising as an effective ingredient an immunostimulant generated by degrading from bacterial cells of an MRE symbiotic bacterial group comprising *Bacillus* sp. (FERM BP-11209), *Lysinibacillus fusiformis* (FERM BP-11206), *Bacillus sonorensis, Lysinibacillus* sp. (FERM BP-11207), and *Comamonas* sp. (FERM BP-11208).

Further, according to one embodiment of the present invention, said immunostimulant in such immune-enhancing composition is composed of at least 98% by weight thereof or more of a hydrophilic low molecular substance of an average molecular weight of not more than 1,000 Da.

Further, according to another embodiment of the present invention, said immunostimulant in such immune-enhancing composition activates macrophages, natural killer cells, or natural killer T cells.

According to another embodiment of the present invention, said immunostimulant in such immune-enhancing composition activates dendritic cells, microglial cells, Langerhans cells, or Kupffer cells.

According to still another embodiment of the present invention, said immunostimulant in such immune-enhancing composition activates epithelial cells, fibroblasts, keratinocytes, or osteoblasts.

According to still another embodiment of the present invention, said immunostimulant in such immune-enhancing composition causes the differentiation and activation of Th17 or Th1.

According to still another embodiment of the present invention, said immunostimulant in such immune-enhancing composition enhances IL-21 production.

According to still another embodiment of the present invention, said immunostimulant in such immune-enhancing composition is preferably obtained by incubating the bacterial cells of said MRE symbiotic bacterial group under culture conditions suitable for growth, placing a resultant culture medium under a starvation condition, and aerating.

Further, according to another embodiment of the present invention, said immune enhancing composition in such immune enhancing composition is used as an anti-inflammatory agent in a subject afflicted with allergic diseases or autoimmune diseases.

In such case, said allergic disease or autoimmune diseases can be selected from the group consisting of temporomandibular arthrosis, ulcerative colitis, atopic dermatitis, and allergic rhinitis.

Moreover, according to another embodiment of the present invention, the immune enhancement composition in such immune enhancing composition is used as adjuvant for vaccines against pathogenic bacteria or pathogenic viruses.

In that case the pathogenic bacteria or viruses can be selected from the group consisting of opportunistic infectious bacteria, HIV, HCV, and HPV.

In addition, according to another embodiment of the present invention, the immune-enhancing composition in such immune enhancing composition is used as a medicine or veterinary drug for treating the subject afflicted with a disease selected from the group consisting of liver cancer, prostate cancer, colon cancer, rectal cancer, lung cancer, pancreatic cancer, stomach cancer, malignant lymphoma, diabetes, hypertension, wound, ligament injury, bone fractures, low temperature burns, acne, floaters, bedsores, and urticaria, or for preventing said disease.

According to another embodiment of the present invention, the immune-enhancing composition in such immune enhancing composition is used as food or feed.

According to the second main aspects of the invention, a method is provided that produces an immune-enhancing composition that enhances a subject's innate immunity by stimulating innate immunity, said method comprising preparing and incubating bacterial cells of an MRE symbiotic bacterial group comprising *Bacillus* sp. (FERM BP-11209), *Lysinibacillus fusiformis* (FERM BP-11206), *Bacillus sonorensis, Lysinibacillus* sp. (FERM BP-11207), and *Comamonas* sp. (FERM BP 11208) and degrading the bacterial cells of said prepared MRE symbiotic bacterial group.

In addition, according to one embodiment of the present invention, said step of degrading in such method is performed by incubating said at least said one bacterium made available under culture conditions suitable for growth, placing the resultant culture medium under starvation conditions, and aerating.

According to the third main aspects of the invention, a method is provided for treating a mammal afflicted with an innate immunity related disease, or for preventing said disease comprising preparing a therapeutically effective amount of an immune-enhancing composition having, as an effective component, an immunostimulant produced by degrading bacterial cells of an MRE symbiotic bacterial group comprising *Bacillus* sp. (FERM BP-11209), *Lysinibacillus fusiformis* (FERM BP-11206), *Bacillus sonorensis, Lysinibacillus* sp. (FERM BP-11207), and *Comamonas* sp. (FERM BP-11208) and administering a therapeutically effective amount of said prepared immune-enhancing composition to the mammal.

In addition, according to one embodiment of the present invention said mammal is a human.

In addition, according to another embodiment of the present invention, said administering step is performed orally.

In addition, according to another embodiment of the present invention, said administering step is performed parenterally.

In that case said parenteral administration step is preferably selected from intravascular administration, injection around or into the tissue, subcutaneous injection, intraocular administration, nasal administration, transdermal administration, and mucosal administration.

According to another embodiment of the present invention, in such method, said innate immunity-related disease can be selected from the group consisting of allergic diseases or autoimmune diseases including temporomandibular arthritis, ulcerative colitis, atopic dermatitis, and allergic rhinitis; pathogenic bacterial- or virus-related diseases including those of opportunistic infectious bacteria HIV, HCV, and HPV; liver cancer, prostate cancer, colon cancer, rectal cancer, lung cancer, pancreatic cancer, stomach cancer, malignant lymphoma, diabetes, hypertension, wound, ligament injury, bone fractures, low temperature burns, acne, floaters, bedsores and urticaria.

Further, the features and characteristic actions and effects of the present invention other those described above will become clear to those skilled in the art by referring to the sections on the embodiments and the drawings of the present invention.

DETAILED DESCRIPTION OF THE INVENTION

Figure 1:
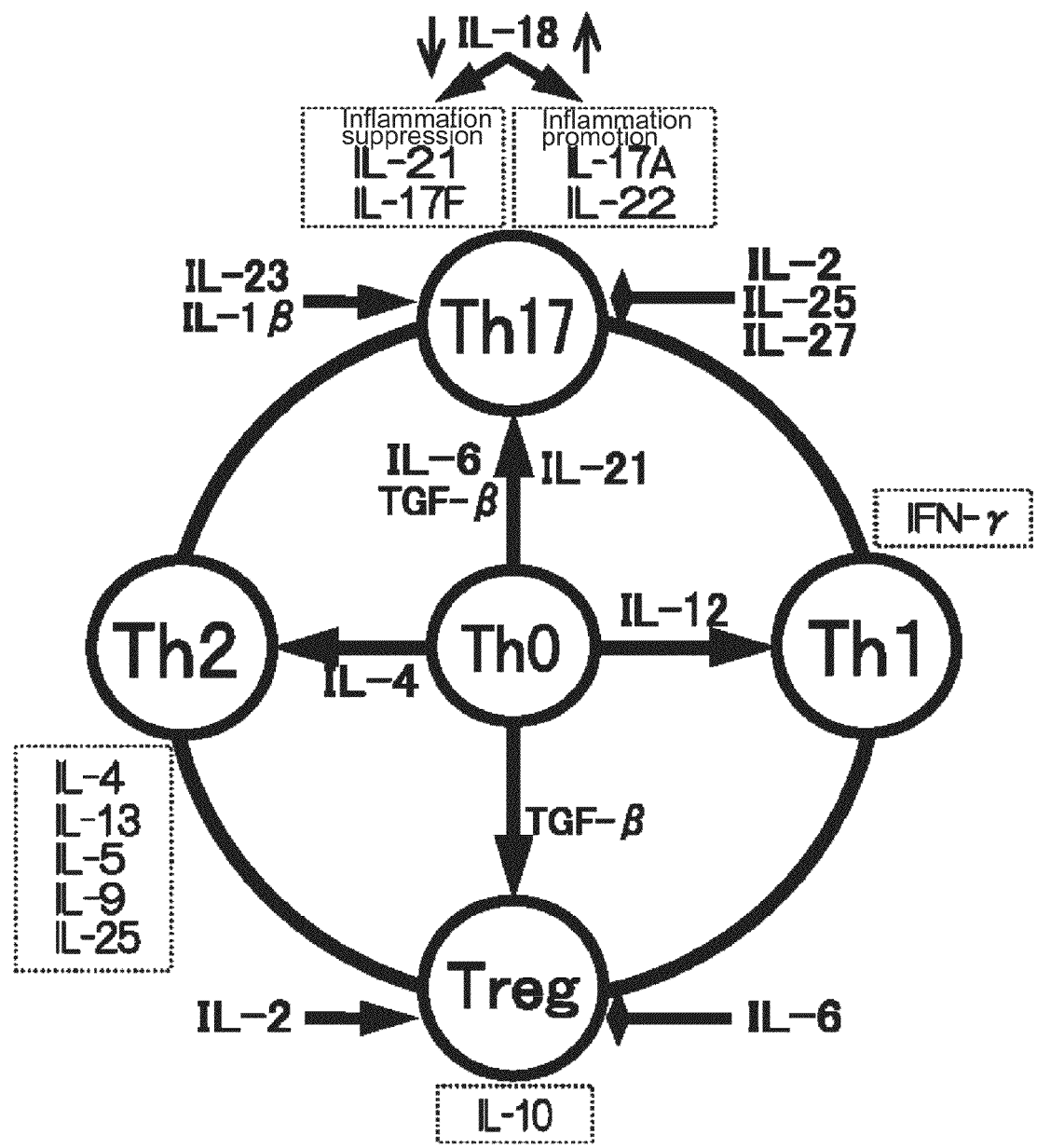
FIG. 1 is a schematic diagram showing a process in which naive cells differentiate into Th17, Th1, Th2, and Treg.

As described above, in accordance with the present invention, an immune-enhancing composition can be provided that effectively enhances immunity functions including innate immunity activity by making use of a low molecular immunostimulant produced by degrading bacterial cells of the MRE symbiotic bacteria group.

Herein, said MRE symbiotic bacteria group consists of *Bacillus* sp. (FERM BP-11209), *Lysinibacillus fusiformis* (FERM BP-11206), *Bacillus sonorensis, Lysinibacillus* sp. (FERM BP-11207), and *Comamonas* sp. (FERM BP-11208), all of which are aerobic bacteria.

As used in the present invention, by "low molecular" is meant a molecule having a molecular weight such that it is permeable through the cell membrane and capable of intracellularly affecting.

More specifically, in accordance with the present invention, a low molecular immunostimulant can be obtained that is cell membrane permeable and composed of bacterial cell degradation products containing low molecular peptides, carbohydrate chains, glycolipids low molecular nucleic acid degradation products, by degradation of bacterial cells of the MRE symbiotic bacteria group comprising aerobic gram-negative bacteria and aerobic gram-positive bacteria with a group of lysosomal enzymes or a group of lysosomal like enzymes.

This immunostimulant, which is cell membrane permeable, reaches out not only to the TLR receptors present on the cell surface, but also to the internal TLR receptors present in the endosomes, phagosomes or the like and microbial sensing NLR receptors and viral sensing RLR receptors, present in the depth of the cells, thereby providing the innate immunity response cells with a profound three-dimensional ligand stimulus.

The immunostimulant obtained by degradation of bacterial cells of the symbiotic bacterial MRE group is composed approximately 99% thereof of a hydrophilic substance with a molecular weight not more than 3,000 and is made up of components such as oligopeptides including MDP-like substances, oligosaccharide chain, single-stranded RNA, thereby providing a low molecular cytotoxicity-free ligand component not available with common digestive enzymes such as so-called protease. This allows the immune-enhancing composition derived from said MRE symbiotic bacteria group to function in vivo as a ligand. In addition, the ligand, a product from a multiple number of mixed bacteria, is multifaceted, simultaneously subjecting the innate immunity receptors to a variety of pattern recognition stimuli. It is the latter aspect that distinguishes the low molecular immune enhancing composition prepared from the MRE symbiotic bacteria group.

Further, in the embodiments and examples in accordance with the present invention described below, the "immune-enhancing composition" derived from the above-mentioned MRE symbiotic composition may for convenience be referred to as "MRE complex ligand" both of which mean the same or is synonymous.

The term "ligand" as used in the present invention refers to a substance that causes the activation of receptors by binding specifically to the immune receptors; complex ligand refers to a mixture or conjugate of multiple ligands. What acts as an adjuvant is also included in the "ligand."

The MRE complex ligand (immune-enhancing composition, hereafter) is capable of stimulating intra- and extra-cellular innate immunity receptors cells into activating immunocytes in the innate immune system, such as macrophages, dendritic cells, Kupffer cells, microglia cells, Langerhans cells, natural killer cells, and natural killer T cells, and epithelial cells on the mucosa and/or skin, fibroblasts, Paneth cells present in the intestinal tract.

In addition, said activation produces a Type I interferon, the release of which then causes the neighboring cells to simultaneously produce therefrom antibacterial and antiviral substances.

In addition, the activation of immunocytes in the innate immune system by the MRE complex ligands in accordance with the present invention causes substances such as interleukin to be secreted into the blood and/or lymph. This allows the T-cell lymphocytes to differentiate and activate into states called Th1 and TH17 that enhance antibacterial, antiviral, and anticancer potency.

Consequently these series of immune activation will ensue promoting in time sequence inflammation suppression and tissue repair processes. In particular, the MRE complex ligand in accordance with the present invention will allow TH17 and the like to produce IL-21 that functions to suppress autoimmunity.

Thus the present invention is capable of providing an immune enhancing composition with a novel low-molecular immunostimulant having antibacterial, antiviral, anticancer, and anti-inflammatory effects as well ensuing autoimmunity suppressive effects thereof, thereby solving the problems described above in accordance with the present invention.

Herein, the present invention is specifically explained, where the instant invention, as set forth above, pertains to a discovery of a group of novel microbial symbiotic bacteria called a MRE symbiotic bacterial group that produces a highly effective immunostimulant by degradation of bacterial cells thereof without high concentration culturing, thereby utilizing it to provide an immune enhancing composition. In addition, the MRE symbiotic bacterial group is made up of five unique bacteria consisting of aerobic gram-positive bacteria and aerobic gram-negative bacteria. These groups of bacteria are not just that of mixture of naturally present bacteria, but are comprised of symbiotic bacteria consisting of 5 unique bacteria, which are bacteria that were the culmination of our continued long term culturing of a variety of soil bacteria along with bacteria adhered to marine products through the initial bacteria's intense competing struggle for survival till uncovering each other's roles in the competition, which bacteria underwent a change in a stable manner through their variation or evolution.

The five bacterial group that makes up the MRE symbiotic bacterial group comprise, aerobic gram-positive bacteria, *Bacillus* sp. (Accession Number FERM BP-11209; Identification Number MK-005 (SEQ ID NO. 5)), *Lysinibacillus fusiformis* (Accession Number FERM BP-11206; Identification Number MK-001 (SEQ ID NO. 1)), *Bacillus sonorensis*, (Identification Number MK-004 (SEQ ID NO. 4)) *Lysinibacillus* sp. (Accession Number FERM BP-11207; Identification Number MK-002 (SEQ ID NO. 2)), and aerobic gram-negative bacteria *Comamonas* sp. (FERM BP-11208; Identification Number MK-003 (SEQ ID NO. 3)).

Herein, Accession Number FERM BP-11206 (transferred from Accession Number FERM P-21548, deposited Mar. 19, 2008), Accession Number FERM BP-11207 (transferred from Accession Number FERM P-21549, deposited Mar. 19, 2008); Accession Number FERM BP-11208 (transferred from Accession Number FERM P-21550, deposited Mar. 19, 2008); and Accession Number FERM BP-11209 (transferred from Accession Number FERM P-21760, deposited Feb. 2, 2009) are the bacteria deposited at International Patent Organization Depository, Advanced Industrial Science & Technology, Japan, an independent corporation.

Next, the characteristics of the "symbiotic bacterial group" in the instant invention are explained. As is well known, mixing and culturing a multiple number of bacteria generates a temporarily unstable state. On the one hand there occurs habitat partitioning based on nutrients in cases like Koji mold (*Aspergillus oryzae*) used in fermentation and yeast fungus (saccharomycete), or *Bacillus subtilis* and other *Bacillus* microbes; on the other hand a fierce struggle for survival unfolds such as intensive competition for organics, attacks one another with free radicals, attacks with peptide type antibiotics by *Bacillus* bacteria, resulting from internal sporulation occurring at a uniform rate even under the rich nutritional value condition, and/or a recently elucidated countering with antibiotics (peptides) by yeast. It is known as much that a period of such a fierce struggle for survival is followed by habitat partitioning based on nutrients, acquisition of resistance to antibiotics, and protection against enzyme denaturation by the release of short-chain peptides capable of removing free radicals and molecular chaperones, and in addition thereto, by exchanging low molecular peptides that help one another's survival and/or growth among completely different types of bacteria. The ultimate goal would be to achieve the overall coexistence and stability of the microorganisms by exchange of each other's capabilities through exchange of genes including the plasmids.

In addition, the MRE symbiotic bacteria group in accordance with the present invention can be grown under any conditions if under viable circumstances; specifically it is possible to grow under culture conditions commonly used in the field of molecular biology. For example, as described below, said bacteria can be incubated in a culture aeration tank, with aeration, in the presence of nutrients: 10 kg fish meal, 10 kg rice bran, 5 kg oil meal, 1 kg of broth along with minerals such as magnesium sulfate, and the like, at pH6.0 to 6.8, and 25° C. to 35° C. incubation temperature, with appropriate aeration. Preferably, said nutrient source is 5 kg fish meal, 5 kg rice bran, oil meal 2.5 kg, and 0.5 kg broth. Further, the culture conditions for the MRE symbiotic bacterial group in accordance with the present invention include, but not limited to, the terms of these settings.

The MRE symbiotic bacteria group in accordance with the present invention has progressed to the stage of active gene exchanging, undergone a mutation, and evolved into an enigmatic bacterial cell body close to bacterial fusion as with the *Bacillus* sp.

Herein described are individual bacteria that make up the MRE symbiotic bacteria group. Respective bacteria that make up the MRE symbiotic bacteria group have the following 16Sr DNAs.

```
[Sequence Listing]

MK-001 (SEQ ID NO. 1)  (Lysinbacillus fusiformis)
TGGAGAGTTT GATCCTGGCT CAGGACGAAC GCTGGCGGCG TGCCTAATAC ATGCAAGTCG  60
AGCGAACAGA GAAGGAGCTT GCTCCTTCGA CGTTAGCGGC GGACGGGTGA GTAACACGTG 120
GGCAACCTAC CCTATAGTTT GGGATAACTC GGGAAACCG GGGCTAATAC CGAATAAYTT 180
GTTTCACCTC ATGGTGAAAC ACTGAAAGAC GGTTTCGGCT GTCGCTATAG GATGGGCCCG 240
CGGCGCATTA GCTAGTTGGT GAGGTAACGG CTCACCAAGG CGACGATGCG TAGCCGACCT 300
GAGAGGGTGA TCGGCCACAC TGGGACTGAG ACACGGCCCA GACTCCTACG GGAGGCAGCA 360
GTAGGGAATC TTCCACAATG GGCGAAAGCC TGATGGAGCA ACGCCGCGTG AGTGAAGAAG 420
GATTTCGGTT CGTAAAACTC TGTTGTAAGG GAAGAACAAG TACAGTAGTA ACTGGCTGTA 480
CCTTGACGGT ACCTTATTAG AAAGCCACGG CTAACTACGT GCCAGCAGCC GCGGTAAT   538

MK-002 (SEQ ID NO. 2)  (Lysinbacillus sp.)
TGGAGAGTTT GATCCTGGCT CAGGACGAAC GCTGGCGGCG TGCCTAATAC ATGCAAGTCG  60
AGCGAACAGA GAAGGAGCTT GCTCCTTTGA CGTTAGCGGC GGACGGGTGA GTAACACGTG 120
GGCAACCTAC CCTATAGTTT GGGATAACTC CGGGAAACCG GGGCTAATAC CGAATAATYT 180
ATTTCAYCTC ATGGTGAAAT ACTGAAAGAC GGTTTCGGCT GTCGCTATAG GATGGGCCCG 240
CGGCGCATTA GCTAGTTGGT GAGGTAAYGG CTCACCAAGG CGACGATGCG TAGCCGACCT 300
GAGAGGGTGA TCGGCCACAC TGGGACTGAG ACACGGCCCA GACTCCTACG GGAGGCAGCA 360
GTAGGGAATC TTCCACAATG GGCGAAAGCC TGATGGAGCA ACGCCGCGTG AGTGAAGAAG 420
GATTTCGGTT CGTAAAACTC TGTTGTAAGG GAAGAACAAG TACAGTAGTA ACTGGCTGTA 480
CCTTGACGGT ACCTTATTAG AAAGCCACGG CTAACTACGT GCCAGCAGCC GCGGTAAT   538

MK-003 (SEQ ID NO. 3)  (Comamonas denitrificans)
TGGAGAGTTT GATCCTGGAC TCAGATTGAA CGCTGGCGGC ATGCCTTACA CATGCAAGTC  60
GAACGGTAAC AGGTCTTTCG GGATGCTGAC GAGTGGCGAA CGGGTGAGTA ATACATCGGA 120
ACGTGCCTAG TAGTGGGGGA TAACTACTCG AAAGAGTGGC TAATACCGCA TGAGATCTAT 180
```

```
                             [Sequence Listing]

GGATGAAAGC AGGGGACCTT CGGGCCTTGT GCTACTAGAG CGGCCGATGG CAGATTAGGT  240
AGTTGGTGGG ATAAAAGCTT ACCAAGCCTA CGATCTGTAG CTGGTCTGAG AGGACGATCA  300
GCCACACTGG GACTGAGACA CGGCCCAGAC TCCTACGGGA GGCAGCAGTG GGGAATTTTG  360
GACAATGGGG GAAACCCTGA TCCAGCAATG CCGCGTGCAG GATGAAGGCC TTCGGGTTGT  420
AAACTGCTTT TGTACGGAAC GAAAAGTCTT GGGTTAATAC CCTGGGATCA TGACGGTACC  480
GTAAGAATAA GCACCGGCTA ACTACGTGCC AGCAGCCGCG GTAAT                  525

MK-004 (SEQ ID NO. 4) (Bacillus sonorensis)
TGGAGAGTTT GATCCTGGCT CAGGACGAAC GCTGGCGGCG TGCCTAATAC ATGCAAGTCG   60
AGCGAACCGA CGGGAGCTTG CTCCCTTAGG TTAGCGCGG ACGGGTGAGT AACACGTGGG   120
TAACCTGCCT GTAAGACTGG GATAACTCCG GGAAACCGGG GCTAATACCG GATGCTTGAT  180
TGAACCGCAT GGTTCAATTA TAAAAGGTGG CTTTTAGCTA CCACTTACAG ATGGACCCGC  240
GGCGCATTAG CTAGTTGGTG AGGTAACGGC TCACCAAGGC GACGATGCGT AGCCGACCTG  300
AGAGGGTGAT CGGCCACACT GGGACTGAGA CACGGCCCAG ACTCCTACGG GAGGCAGCAG  360
TAGGGAATCT TCCGCAATGG ACGAAAGTCT GACGGAGCAA GCCGCGTGA GTGATGAAGG   420
TTTTCGGATC GTAAAACTCT GTTGTTAGGG AAGAACAAGT ACCGTTCGAA CAGGGCGGTG  480
CCTTGACGGT ACCTAACCAG AAAGCCACGG CTAACTACGT GCCAGCAGCC GCGGTAAT    538

MK-005 (SEQ ID NO. 5) (Bacillus sp)
TGGAGAGTTT GATCCTGGCT CAGGATGAAC GCTGGCGGCG TGCCTAATAC ATGCAAGTCG   60
AGCGAATGGA TTAAGAGCTT GCTCTTATGA AGTTAGCGGC GGACGGGTGA GTAACACGTG  120
GGTAACCTGC CCATAAGACT GGGATAACTC CGGGAAACCG GGGCTAATAC CGGATAACAT  180
TTTGAACYGC ATGGTTCGAA ATTGAAAGGC GGCTTCGGCT GTCACTTATG GATGGACCCG  240
CGTCGCATTA GCTAGTTGGT GAGGTAACGG CTCACCAAGG CAACGATGCG TAGCCGACCT  300
GAGAGGGTGA TCGGCCACAC TGGGACTGAG ACACGGCCCA GACTCCTACG GGAGGCAGCA  360
GTAGGGAATC TTCCGCAATG GACGAAAGTC TGACGGAGCA ACGCCGCGTG AGTGATGAAG  420
GCTTTCGGGT CGTAAAACTC TGTTGTTAGG GAAGAACAAG TGCTAGTTGA ATAAGCTGGC  480
ACCTTGACGG TACCTAACCA GAAAGCCACG GCTAACTACG TGCCAGCAGC CGCGGTAAT   539
```

TABLE 1

Table of MRE symbiotic bacteria group properties

| | | Bacteria ID | | | | |
|---|---|---|---|---|---|---|
| | | MK-001 | MK-002 | MK-003 | MK-004 | MK-005 |
| Assigned classification | | *L. fusiformis* | *Lysinibacillus* | *Comamonas* | *B. sonorensis* | *Bacillus* sp |
| Cell form | | *Bacillus* | *bacillus* | *bacillus* | *bacillus* | *bacillus* |
| Size | | 0.7-0.8 × 1.5-2.0 | 0.6-0.7 × 1.5-2.5 | 0.6-0.7 × 1.5--2.0 | 0.7-0.8 × 1.5-2.0 | 1.0-1.1 × 1.5-2.5 |
| Gram stain | | + | + | − | + | + |
| Spore formation | | + | + | − | + | + |
| Motility | | + | + | + | + | + |
| Culture temperature | | 30° C. | 30° C. | 30° C. | 30° C. | 30° C. |
| Culture growth at 37° C. | | + | + | + | + | + |
| Culture growth at 45° C. | | + | + | − | + | + |
| Catalase reaction | | + | + | + | + | + |
| Oxidase reaction | | + | + | + | − | + |
| Colonization time | | culture 24 h | culture 24 h | culture 24 h | culture 24 h | culture 24 h |
| Colony morphology | Diameter | 1.0-2.0 mm | 2.0-3.0 mm | 1.0-2.0 mm | 2.0-3.0 mm | 2.0-3.0 mm |
| | Color | cream colored | cream colored | light yellow colored | cream colored | cream colored |
| | Shape | Circular | circular | circular | irregular | circular |
| | Asperity | Flat | flat | lenticular | flat | flat |
| | Edges | Wavy | wavy | wavy | stringy | wavy |
| | Surface condition | Smooth | smooth | smooth | smooth | opaque |
| | Transparency | Opaque | opaque | opaque | opaque | opaque |
| | viscosity | butter-like | butter-like | butter-like | viscid | butter-like |

In the present invention, these MRE symbiotic bacteria can be cultured in the same way as with conventional aerobic bacteria. It can be done both in aerated culture plates of general agar culture (Nutrient Aga) and in the aerated liquid container.

[Method of Bacterial Cell Degradation]

Herein, now, explained below are two methods for bacterial degradation of the MRE symbiotic bacterial group according to the present invention thereby obtaining a low molecular MRE complex ligand.

The first method is that of degrading the MRE symbiotic bacteria group with a group of lysosomal enzymes thereby obtaining a low molecular complex ligand.

The second method is that of obtaining a low molecular complex ligand by degrading MREE symbiotic bacteria group with primitive lysosomal homologous mother cell lytic enzymes that appear in the step of spore formation of the MRE symbiotic bacteria group The reason for using these methods is that catabolic enzymes such as ordinary digestive enzymes and common proteases fail to provide ligands with molecular weights required to permeate the cell membrane.

In contrast, a group of enzymes that are secreted in the animal lysosomes, plant vacuoles, fruits, and the like and that have the ability to degrade the cell organelles and polymeric substances in bulk down to low molecular substances. The lysosomal enzymes are enzymes involved in autophagy that breaks down aged organelles in cells and rejuvenates them and those that appear at the final stages where cancer cells and/or viral infected cells undergo apoptosis, which are particularly known to be active when degrading the bacteria that invaded into the cell in endosome cells.

Said homologous enzyme group is known to emerge in a process of autophagy and/or apoptosis in animals, plants, and microbes. This is also a group of enzymes called processing enzymes in plants that emerge within the vacuoles or during fruit formation. These groups of enzymes would break down the bacterial cells down to low molecular substances small enough to be permeable through the cell membrane.

For the lysosomal enzymes in accordance with the present invention, not fewer than 50 catabolic enzymes can be used, including nucleases such as ribonuclease, and deoxyribonuclease, and the like; proteolytic enzymes having powerful and versatile capabilities such as collagen-degrading enzyme cathepsin L, aspartic proteases cathepsin D and cathepsin E; cysteine proteases cathepsin K, cathepsin B, and cathepsin S; serine protease cathepsin G; aminopeptidase cathepsin H, and the like; arylsulfatase, β-glucuronidase, esterase, and acid phosphatase; carbohydrate chain degrading enzymes such as sphingolipid-degrading α-galactosidase, β hexosaminidases A and B, allyl sulfatase A, galactosylceramidase, glucosylceramidase, acid sphingomyelinase, acid ceramidase, and the like; glycoprotein-degrading α-fucosidase, α- and β-mannosidases, neuraminidase, aspartylglucosaminidase, N-acetyl galactosaminidase; mucopolysaccharide-degrading α-iduronimidase, iduronatesulfatase, heparanNsulfatase, α-N-acetylglucosaminidase, 6-sulfatase, galactose 6-sulfatase, β-galactosidase, allylsulfatase B, β-glucuronidase; and the like; lipolytic enzymes degrading cholesteryl esters and fat such as acid lipase; and more importantly muramidase, mucopeptide hydrolase, and the like that degrade the peptidoglycan layer that forms the cell wall of pathogenic prokaryotic microorganisms. In addition, use can be made of papain or the like, which is a lysosomal homologous cathepsin K-like enzyme of green papaya.

These lysosomal enzymes are active when slightly acidic (pH6.3 to pH6.8) with their activity elevated at high temperature range (38° C. to 42° C.) where the activity of ordinary digestive enzymes is suppressed. Furthermore, among them are many having high degradation potency, some having the potency as high as 5,000 to 10,000 times that of the ordinary digestive enzymes.

The first method to obtain an MRE complex ligand from the MRE symbiotic bacterial group in accordance with the present invention is one which uses a combination of a cell wall-lytic enzyme and cathepsins from among these lysosomal enzymes with a nuclease.

For the cell wall-lytic enzymes, use is made of muramidase, mucopeptide hydrolase, and the like; for the cathepsins, cathepsin B, cathepsin D, cathepsin L, cathepsin K, or papain; for the nucleases, ribonuclease, and deoxyribonuclease. While these enzymes can be created by gene recombination into a plasmid or DNA, they can also be obtained by having fishes (including eel) autolyzed under sterile conditions at elevated temperatures (38° C. to 45° C.), in a moist environment. They can also be obtained by using a group of lysosomal enzymes produced when fruits such as papaya ripen.

However, while the first method is advantageous in that the bacterial cell degradation can be adjusted by changing the enzyme blend ratio, it is disadvantageous in that the enzymes are currently expensive and it is difficult to handle them in some cases requiring special equipment, thereby making this method costly.

A second method to obtain a low-molecular complex ligand from the MRE symbiotic bacteria group is one which uses, as is, a primitive mother cell lytic enzyme released during the spore formation step. Although the enzyme blend cannot be varied, excellent ligands can be mass produced at a very low cost. This method is one for obtaining a low-molecular complex ligand using the mother cell lytic enzymes released in connection with spore formation of the MRE symbiotic bacteria group.

Furthermore, "mother cell lytic enzyme group" or "mother cell lytic enzyme" as used in the present invention refers to the lysosomal homologous enzymes produced during a spore formation step of bacterial cells.

Preparation of a low molecular MRE complex ligand in accordance with the present invention calls for, at its first stage, charging a blend culture medium with a MRE symbiotic bacterial group and incubating under the culture conditions involving the addition of, as bacterial nutrients, fish meal, rice bran, oil cake, broth and the like, minerals such as magnesium sulfate, at a culture pH 6.0 to 6.8 and a culture temperature at 25° C. to 35° C., along with sufficient aeration (aeration: 0.1 mg/L to 1.0 mg/L dissolved oxygen concentration). After the growth and stabilization of the MRE symbiotic bacterial group is attained, the system is placed under a starvation condition with the nutrients cut off, followed by continued aeration, whereupon the depletion of nitrogen components triggers a sporulation (internal sporulation). In this case, a stable quality product can be obtained if the vegetative cells prior to sporulation are transferred to another aeration tank. In this manner it is made possible to degrade the bacterial cells of the MRE symbiotic bacteria group down to low molecular products.

The bacterial cell degradation process in accordance with the present invention is further detailed, wherein blended bacterial cells which have built mutual bacterial symbiotic relationships and reached a stable symbiotic body's vegetative cell state, along with the culture containing digestive enzymes secreted from the vegetative cells thereof, are separated into another aerating culture vessel. Aeration is continued in the aerating culture tank with no nutrients other than silica. Autophagosomal homologous mother cell lysis of the MRE bacterial group in a symbiotic state begins, and the bacterial vegetative cells undergo bulk degradation and vanish while releasing lysosomal homologous mother cell lytic enzymes. On confirmation of the completion of the sporulation, aeration (oxygen supply) is stopped; then spores simultaneously begin to precipitate, providing a transparent supernatant liquid. The resultant supernatant liquid is pressure filtered through a 0.2 μm membrane, to remove the remaining spores, followed by further removing micro-spores and/or impurities through a 0.02 μm filter. Thus, this allows harvesting an effective low molecular MRE complex ligand by making use of the mother cell lytic enzymes formed during the sporulation of MRE symbiotic bacteria group. Moreover, continuous production is also feasible by devising a separation process.

Thus the MRE symbiotic bacteria group permits a sufficiently effective MRE complex ligand to be prepared even without high concentration production, but it is also possible to carry out high concentration production. In the latter case, repetitious formation of vegetative cells and sporulation results in the vegetative cells absorbing the complex ligand, adversely affecting the yield and in an increase in the production of antibiotics, such that it is important to perform the sporulation all at once after a high density culturing. It is known that providing a silica nutrient further improves efficiency.

The product obtained by sporulation all at once was essentially free of any antibiotics, below a detectable level.

The low molecular complex ligands prepared in this manner contain oligopeptides, single-strand RNA degradation products, oligosaccharides, glycolipids and MDP (muramyl dipeptide)-like substances, and flagellin degradation products, having a molecular weight distribution as shown below.

Table 2 below shows the molecular weight distribution of a MRE complex ligand.

TABLE 2

Molecular weight distribution of MRE complex ligand

| Range of molecular weight | Peak area (%) |
|---|---|
| Not lower than 10,000 | Trace |
| 3,000 to 10,000 | Trace |
| 1,000 to 3,000 | 1.5% |
| 500 to 1,000 | 1% |
| Not higher than 500 | 97.5% |
| Total | 100% |

Thus the MRE complex ligand of this invention, not less than 98% thereof, is composed of hydrophilic low molecular substances, 1,000 or less, including oligopeptides, oligosaccharide chains, oligo level nucleic acids, oligo level glycopeptides and glycolipids. The resultant low molecular complex ligand obtained in this way, has no toxicity, such as an endotoxin, and being low molecular makes it free from a direct antibody attack.

The MRE complex ligand is such that even with an endotoxin test capable of detecting the presence of LPS and peptidoglycan, their presence was below the detection limit, demonstrating the absence of the LPS and peptodiglycan. In addition, it was found that even a cell dysfunction test used for performing an activity test for macrophages, natural killer cells, and the like showed that there was no cell dysfunction up to the limiting concentration at which a breakdown occurs due to osmotic pressure. In addition, said ligand also has cleared an acute toxicity test using a rabbit.

Making such a low molecular ligand not only provides an advantage of offering a very toxicity-free ligand, but also permits the ligand to be absorbed through the intestine and the mucosa, thereby presenting the important advantage of allowing the ligand to be efficiently ingested as a beverage. The product, being hydrophilic and having a molecular weight in an oligo range, makes it theoretically possible to be absorbed through the skin.

Next, in order to clarify the innate immunity activity by the MRE complex ligand of the instant invention and the ensuing series of immune processes, a comprehensive DNA kinetic analysis via a DNA microarray and a real-time PCR confirmation test, using human macrophages were conducted.

In addition, a group of immunocytes in the human blood (macrophages, dendritic cells, Langerhans cells, NK, cells NKT cells T cell group, B cell group and the like) was separated; and the production of each cytokine by the MRE complex ligand was examined using an antibody.

The stock solution containing the MRE complex ligand as used contains 80 μg/ml of the MRE complex ligand-containing low molecular components.

As a preliminary test, the amount of TNF-α production was determined using real-time PCR, resulting in the production 90.46 times the normal level as shown in Table 3. Herein, Med stands for no stimulus. LPSp is for an endotoxin stimulus; MRE 1/10 is for a 10-fold dilution of the MRE complex ligand-containing stock solution; and the same thereafter for 100- and 1000-fold dilutions. The LPSp concentration for comparison is 100 ng/ml.

TABLE 3

Macrophage's TNF production

| Specimen type | Relative magnitude of expression | Standard deviation | Ratio |
|---|---|---|---|
| Med | 2.13 | 0.84 | 1.00 |
| LPSp | 25.57 | 4.68 | 12.00 |
| MRE 1/10 | 192.68 | 102.94 | 90.46 |
| MRE 1/100 | 9.22 | 5.64 | 4.33 |
| MRE 1/1000 | 2.28 | 0.55 | 1.07 |

Figure 4:
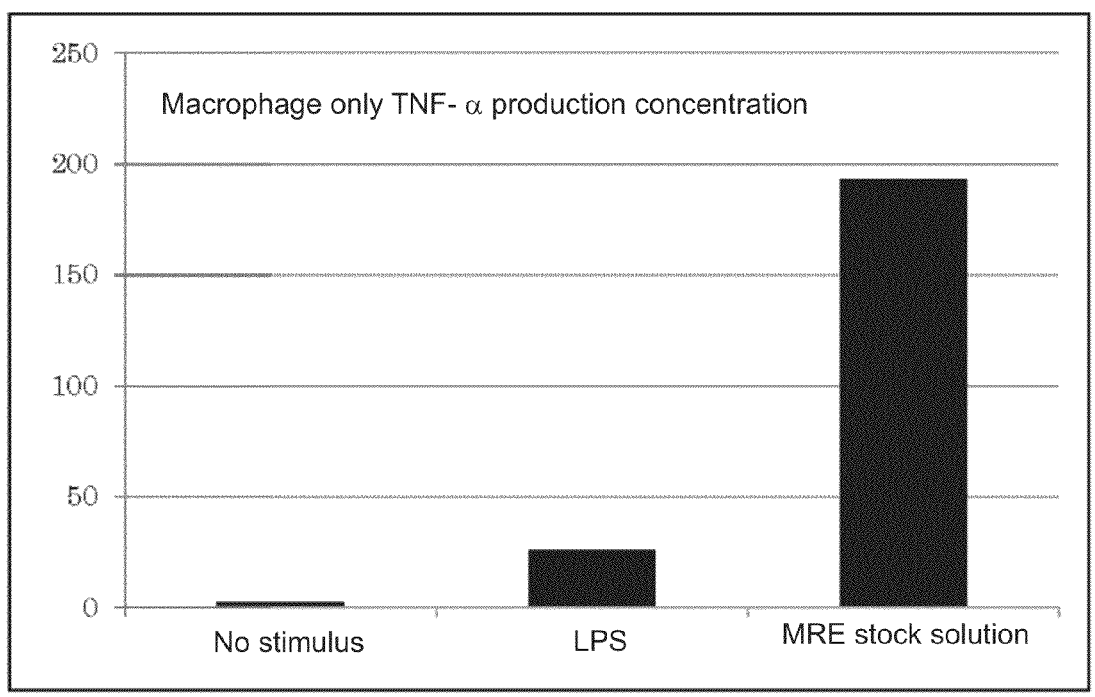
FIG. 4 is a TNF-α production trial graph with macrophage alone. It compares a TNF-α production concentrations with no stimulant (Control) and with the addition of LPS IL and a 6% dilute solution of the MRE beverage.

Thus with macrophages alone, when stimulated with a 10-fold diluted solution of the stock containing the MRE complex ligand gave a TNF-α production 90.4 times the normal level, even amounting to 7.5 times relative to LSPs used for a comparison. This demonstrates that the MRE complex ligand has high macrophage activation potency. (See FIG. 4).

On the other hand, there is a need to note that just because the production of TNF-α is high does not mean that inflammation is promoted. These data merely reflect high macrophage activation potency.

That is because what has emerged from the current comprehensive DNA kinetic analysis indicates that living organisms manage their immunity process in a wave-like manner striking a balance in expressing an inflammatory substance while simultaneously releasing a little inflammatory suppressant.

There is a piece of evidence, as shown in Table 4, that there was no TNF-α production when stimulation occurs with the stock solution containing the MRE complex ligand using human blood containing various immunocytes; this has also been confirmed in many clinical trials that in contrast, the ligand provides anti-inflammatory effects.

TABLE 4

TNF-α production in the blood (ng/ml)

| Test subjects | Control | MRE complex ligand |
|---|---|---|
| A | 34.3 | 36.5 |
| B | 221.8 | 214.9 |
| C | 617.9 | 549.2 |
| D | 77.5 | 83.3 |
| E | 21.5 | 225.4 |
| Average | 232.8 | 221.8 |

This demonstrates that it is necessary to evaluate the ligand effects and/or adjuvant effects through the overall immunizing process and that it is no longer valid to argue that something is effective merely because a certain ligand produced a certain cytokine.

The MRE complex ligand activates the immunizing process involving innate immunity activation and the ensuing antiviral, antibacterial, anti-inflammatory effects, and tissue repair thereby restoring the living body back to normal. It could be something called a breakthrough ligand or adjuvant.

The process, ranging from this innate immunity activation to lymphocyte activation, and an anti-inflammatory effect, and to tissue repair is now detailed in a chronological order.

A. Activation of the Innate Immune Receptors (TLR, NLR, and RLR)

It was confirmed by a comprehensive DNA kinetic analysis that the MRE complex ligand activates a group of NLR innate immune receptors including TLR-2, TLR-7, TLR-8, and NLR-2, which are innate immunity receptors. TLR-2, which is an innate immunity receptor present on the cell surface, senses Gram-positive bacterial peptidoglycan, lipoteichoic acid, lipoprotein, viral glycoprotein, fungal polysaccharides, and the like. Active in the MRE complex ligand is an MDP-like peptidoglycan degradation product having a molecular weight of not more than 1000.

TLR-7 and TLR-12, both present in the cell endosomes, are receptors for sensing single-stranded RNA and also for sensing a low molecular substance from bacterial cell degradation of bacteria and/or viruses. The MRE low-molecular complex ligand of the present invention is thought to sense single-stranded RNAs having a molecular weight of not more than 1000. This fact means that the present invention can be expected to have a high adjuvant effect against RNA viruses.

In addition, NLRs including NLR-2, which are primitive receptors present intracellularly, are able to detect low-molecular bacterial or viral degradation products. In particular, NLR-2 is a receptor that expresses specifically to APCs (antigen presenting cells) such as macrophages, dendritic cells, Langerhans cells, and Kupffer cells. The group of NLR receptors activated by the MRE low molecular complex ligands can sense MPD-like substances and the like low molecular ligands. This again permits one to expect the ligand to operate very effectively as an adjuvant.

Thus it can be discerned the MRE low molecular complex ligand of the invention are sensed three dimensionally by three innate immunity sensors, which are receptors present on the cell surface, receptors present in the endosomes, and receptors present intracellularly.

B. Macrophage Activity and Natural Killer Cell Activation

Next, macrophage activity, a main player of animal innate immunity, natural killer cell activity, and IL-8 production from the macrophage that induces neutrophil migration, by the MRE compound ligand were confirmed. Neutrophils are one of the innate immunity phagocytes.

According to the data from a macrophage activation test with an MRE complex ligand, the NO production capability with an unstimulated culture medium is 0.446 μM, while the production capability with a 10 fold diluted solution of the MRE complex ligand-containing stock solution is 24.059 μM, a value greater than that of 18.712 μM obtained with a 0.1 ng/ml LPSp solution.

More importantly, the viable cell count falls with an increasing concentration of LPS, as shown in Table 5, whereas with the MRE complex ligand, the viable cell count increases as its concentration increases. This is an outstanding aspect for the MRE complex ligand, also indicating that when the ligand is used as an adjuvant, the immunity is enhanced while the viability of the immune cells is increased, making its use advantageous.

TABLE 5

Human macrophage activity test

| Specimen used for determination | Concentrations/ dilution | Viable cell count index |
|---|---|---|
| Culture alone | 0 | 1.12 ± 0.07 |
| LPS (endotoxin) | 0.001 μg/ml | 1.64 ± 0.02 |
| LPS (endotoxin) | 0.1 μg/ml | 1.47 ± 0.15 |
| MRE complex ligand (Composition of the instant application) | 3,000-fold dilution | 1.74 ± 0.10 |
| MRE complex ligand (Composition of the instant application) | 30-fold dilution | 2.47 ± 0.15 |

This macrophage cell viability test entailed determining the macrophage plate adhesion ratio as an index for the viable cell count by staining with crystal violet and measuring the absorbance at 570 nm.

In addition, as will be described later, also with natural killer cells, an NK activation test for the MRE complex ligand-containing stock solution using human blood gave a result on average 1.73-fold (562/Very High) [that of the normal].

C. Switching Process According to the Pattern Thereof from Innate Immunity Receptor Stimulation When an ligand and/or adjuvant stimulates innate immunity receptors such as TLR, NLR, and RLR, this induces activation of cells, which at the same time is followed by switching via a variety of patterns to 3 types of processes: "antiviral substance production process," "inflammation onset and delayed type inflammation suppression process" (antibacterial, anticancer, and inflammation repair process), "process to apoptosis."

It has been revealed by a comprehensive DNA kinetic analysis that when the MRE complex ligand in accordance with the present invention acts on the target, the two former processes take place and the "process to apoptosis" has been blocked.

"The process to apoptosis" is the process that gives rise to a cascade of apoptosis, in which FADD triggers apoptosis, leading to activation of caspase 8 enzyme and/or caspase 10 enzyme, and induction of apoptotic degradation enzymes such as cathepsin D and cathepsin B, which are execution unit enzymes It was confirmed in the present invention that the expression of apoptosis-inducing genes APIs is at a normal level; apoptotic suppression gene JUN is expressed (6.77409 times the normal level); and also expressed is gene SOD2 (8.99963 times the normal level) that guards against the release of apoptosis-inducing cytochrome C from the mitochondria, thereby blocking apoptosis.

D. Process to the Production of Type I Interferon from Innate Immunity Receptor Stimulation "The antiviral substance production process" is one of the processes of original innate immunity, in which a cascade of process activation steps propagates: stimulation of TLR 3, TLR7, TLR8, and RGR leading to the expression of TRAM and TRIF, followed by IKK activation, and activation of IRAK 3, IRAK 7 and the like, resulting in the production of Type I IFN-α (now 13 types are known) and IFN-β to be released extracellularly. This process is believed to be a mechanism built in the unicellular age; in humans, the release of these interferons causes a concurrent release of ISG antiviral substances (several hundred types are known) from neighboring cells such as epithelial cells and mucosal cells.

This process is an original role of innate immunity and is known to have a different combination of ISGs, which are antiviral substances produced dependent on the stimulation pattern. For example, influenza leads to the release of antiviral substances such as IFIT1, G1P3, G1P2, OAS1, M1X1, IFIH1, IFIT3, RIG-I, GBP1, LAMP3, IRF7, ISGF3G, WARS, PSMBS6, BTC, SOCS1, and SERPING 1 thereby exhibiting antiviral effects in response to viral mutation. The MRE complex ligand, by having been activated prior to this process, makes it possible to produce type I interferon immediately and powerfully when the host is infected with viruses such as influenza, thereby effectively reinforcing antiviral potency. In other words its adjuvant effect is at a very high level.

The innate immune receptor stimulation by the MRE complex ligand, in the absence of virus, was confirmed to actually cause type I interferon to be produced as shown below:

Table 6 reveals how much type I interferon gene expression increases with the MRE complex ligand, in the absence of viral infection, using a comprehensive DNA kinetic analysis.

TABLE 6

Type I Interferon production (MΦ)

| IL28a | 1.84637 | IFN-λ |
| ILNA6 | 1.67936 | IFN-α |
| IFN5 | 1.27655 | IFN-α |
| IFNB1 | 1.41305 | IFN-β |

Thus the MRE complex ligand is seen to give significant increases in IFN-α and IFN-β.

Figure 3:
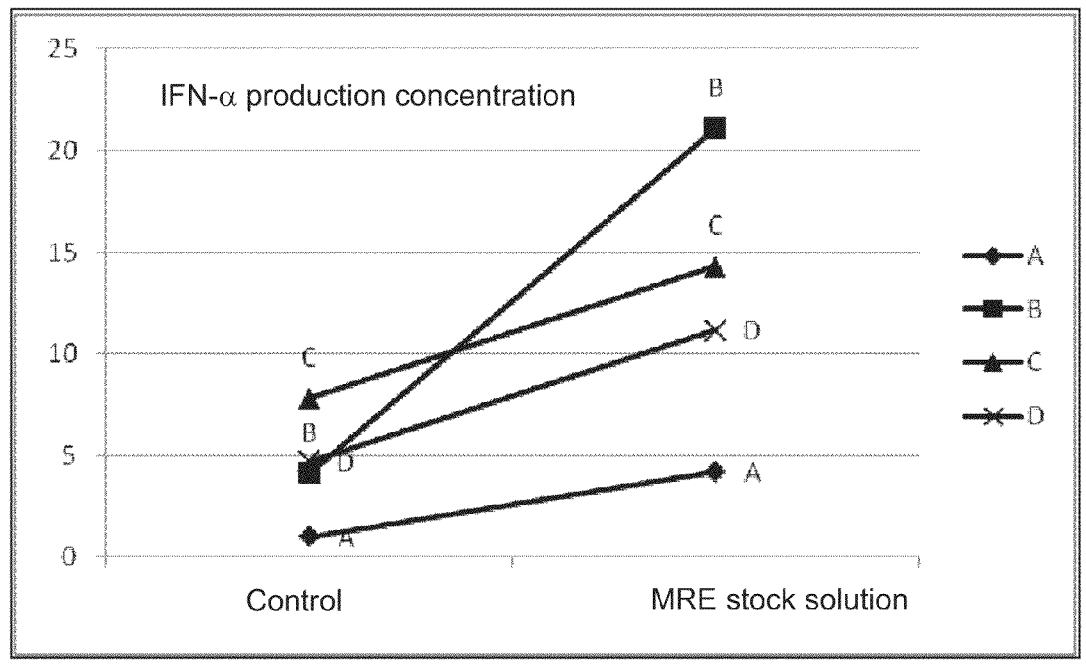
FIG. 3 is an IFN-α production trial graph using human blood. It compares IFN-α production concentrations among four subjects A to D with no stimulant (Control) IL and with the addition of a 6% dilute solution of the MRE beverage.

As will be described later, also in the measurement of type I interferon production by the MRE complex ligand using freshly drawn human blood, the IFN-α production also has further increased. (See FIG. 3) As just described herein, the MRE complex ligand is believed to have no side effects as an antiviral adjuvant.

The MRE complex ligand stimulation of macrophages led to a direct expression of antibacterial genes, as in Table 7.

TABLE 7

Antibacterial substance production (MΦ)

| PTX3 | 7.26891 | Diffensin |

Although this process has not been elucidated, the process in which the antibacterial substance is released directly with no mediation of Th17 cells appears to be also similarly activated.

Also similarly activated in these processes are macrophage-sibling dendritic cells, microglia cells, Kupffer cells, Langerhans cells, fibrosis cells as well as epithelial cells and keratinocytes that express the same innate immunity receptors, and in addition, innate immunity response cells located in each of the organs including the trachea, the gastrointestinal tract, and the urinary tract.

E. Inflammation Onset and Delayed-Type Inflammation Suppression=Antibacterial Anti-Cancer, and Inflammatory Repair Processes This process is the process from the innate immunity receptor stimulation to production of interleukins that stimulate T cells, which is made up of the following two-stage process:

In the first stage process, stimulation of TLR receptors undergoes through processes involving activation of MYD 88, IRAK1 and IRAK4, TRAF6 and the like, followed by separation of I-κB from NF-κB and activation of NF-κB.

Also in the NLR receptors, when stimulated with a ligand, the NLR receptor pairs and RICK binds thereto through mediation of NLR's CARD, leading to ubiquitination of the RICK, followed by further binding of complexes such as TAK1, MEMO, and the like, thereby activating IKKβ, separating I-κB from NF-κB, and activating NF-κB.

The resultant activated NF-κB along with AP-1 binds to DNA, functioning to produce chemokines including IL-1β, TNF-α, and IL-8. At the end of the first stage, there occurs a transition to the second stage by producing IκB-ζ, the second step trigger.

In the second stage process: IκB-ζ joins NF-κB and AP-1 which operate on DNA, thereby producing IL-12p40, IL-6, and others, resulting in control of the T lymphocyte immunity.

Table 8 shows the results from a comprehensive DNA kinetic analysis of the first stage process of gene expression when stimulated with the MRE complex ligand using human macrophages. This result is also consistent with that from a real-time PCR analysis.

The moment in the first stage activation process by the MRE complex ligand in which vigorous production of chemokines including IL-1β, TNF-α and IL-8 is ongoing is captured here, showing a situation where there is an increase in the activation drive of a group of anti-inflammatory genes that suppresses the operation of NF-κB, which starts delayedly to the inflammatory process, resulting in the means by which the NF-κB gene expression has come to fall off.

Then, JUN and/or SOD2 are expressed to block TNA-α and the like from inducing apoptosis of the host's own cells, so as to prevent, with SOCS3, the inflammation from progressing excessively in response to more-than-necessary stimuli from the innate immunity receptors.

Because the control system functioned well, PDLIM, capable of ubiquitinating and degrading excess NF-κB, did not need to operate so that it was at a normal level of 1.0721337.

The moment at which IκB-ζ abruptly rose that holds the key to a phase-in from the first to second stage was captured.

TABLE 8

NF-κB activation (first stage)

| NFKB1 | 2.79457 | NF-κB active |
| NFKB2 | 2.53403 | NF-κB active |
| APIM2 | 1.29901 | DNA control |
| AP1S2 | 1.28658 | DNA control |
| IL1B | 47.6414 | IL-1 production |
| TXF | 21.1826 | TNF-α production |
| IL-8 | 20.4317 | Chemokine production |
| JUN | 6.77408 | Apoptosis suppression |
| SOD2 | 8.99963 | Apoptosis inhibition |
| SOCS3 | 2.62260 | Inflammation control |
| NFKBIZ | 20.0115 | IκB-ζ |

Delayed-Type Inflammation Suppression

Expressed are delayed type inflammation suppressor genes that suppress inflammation delayedly to the first stage. These genes suppress the operation of NF-κB and AP-1. The current analysis with the MRE complex ligand revealed that an inflammation suppression process proceeds delayedly to the inflammation process.

TABLE 9

Suppression of NF-κB and AP-1 operation

| TNFAIP6 | 37.0424 | Strongly anti-inflammatory action |
| TNFAIPS | 18.8303 | Suppression of NF-κB etc. |

TABLE 9-continued

| Suppression of NF-κB and AP-1 operation | | |
|---|---|---|
| NFKBIA | 8.42561 | I-κB production |
| NFKBID | 2.10104 | I-κB production |
| IKBKE | 1.4477 | I-κB production |
| NLRP4 | 1.35103 | Suppressing NF-κB |
| JUN | 6.77408 | Apoptosis suppression |
| SOD2 | 8.99963 | Apoptosis inhibition |
| SOCS3 | 2.62260 | Inflammation control |
| PDLIM2 | 1.07213 | Degrading NF-κB |

Herein, as shown in Table 9, TNFAIP6 is a gene that strongly suppresses NF-κB, has a strong anti-inflammatory action that controls the TNF-α production, and expresses at a high value of 37.0424 times the normal level. TNFAIP3 is also a gene that suppresses the expressions of NF-κB and AP-1 and has also a high value of 18.8308. In addition, the fact that JUN, SOD, SOCS3 are operating is as was already described.

The second stage process is triggered by I-κB-ζ (trigger). Since a large number of NF-κB and AP-1 are already in operation as bound to nucleic acids, delayed inflammation suppression genes are made more active thereby diminishing the fresh supplies of NF-κB and AP-1.

The newly-created IκB-ζ triggers and binds to the NF-κB which is already bound to nucleic acids and together with AP-1 which is similarly already bound to nucleic acids, produce and secrete four groups of cytokines that control T cells. As for macrophages and the like, the M1 activation produces cytokines "IL-12p40," "IL-6 and IL-23p19"; M2 activation, "IL-4," "TGF-β, "IL-2" and the like. This is followed by binding to p35, which is constantly being produced intracellularly, thereby turning IL-12p40 into TL-12 and IL-23p19 into IL-23.

Table 10 shows how the gene expression takes place, starting the second stage by stimuli with the MRE complex ligand. At the moment of the analysis, the I-κB-ζ trigger rapidly increased to 20.015 times the normal level and the NF-κB and AP-1 had their production fall by virtue of the enhanced expression of inflammation suppression genes.

TABLE 10

| IL-12 and IL-34 Production (Start of Second Stage) | | |
|---|---|---|
| NFKBIZ | 20.0115 | I-κB-ζ trigger |
| NFKB1 | 2.79457 | NF-κB remains or adds |
| NFKB1 | 2.53403 | NF-κB remains or adds |
| AP1M2 | 1.29901 | NF-κB remains or adds |
| AP1S2 | 1.28658 | NF-κB remains or adds |
| IL-6 | 1.40574 | Differentiation into Th17 |
| IL-23A | 1.78493 | Activation of IL-23p19/Th17 |
| IL-12B | 1.83736 | Activation of IL-12p40/Th1 |
| TGFβ 1-3 | 0.9802 to 0.7367 | Differentiation of Treg |
| IL-4 | 1.00000 | Differentiation and activation of Th12 |

However, since NF-κB and AP-1 with reduced expressions have already bound to nucleic acids (DNA), a rapid rise in the IκB-ζ expression leads to the starting of the production of IL-6, IL-23p19, and IL-12p40, which at 1.4 to 1.8 times the normal, begin to rise. As seen from this result, the M-1 activation is clearly expressed with the MRE complex ligand. This is also corroborated from the fact to be described later that the IL-23 production from the blood of a person who used the MRE complex ligand is 2.11 times the normal level.

Thus, the MRE complex ligand brings macrophages and siblings thereof such as microglia cells, dendritic cells, Langerhans cells, Kupffer cells, and the like to M1 activation, thereby exerting antibacterial and antiviral effects. It also invigorates phagocytic activity on apoptotic cancer cell debris.

It is usually believed that when bacterial cells and viruses are degraded to low molecular products and removed, as a result of antibacterial and antiviral actions due to M1 activities, the macrophage M1-activity, when signaled by the bacterial and/or viral low molecular degradation products, switches to M2 activity. M2 activity is the post-treatment process for suppressing inflammation and activating fibroblasts so as to repair the tissues destroyed by inflammation and the like. In light of the Examples it is suggested that also in M2 does the MRE complex ligand play important roles.

In addition it has been revealed in the finding to be described later that the MRE complex ligand has excellent properties in that apart from the conventional M1 activity processes of expressing antibacterial, antiviral or anticancer actions, it permits concurrently running an anti-inflammatory process with inflammatory diseases including allergic diseases and autoimmune diseases.

F. T Cell Differentiation with the MRE Complex Ligand and Process Activation Thereafter.

The four sets of cytokines released from activated macrophages and siblings thereof, as shown, in FIG. 1, control the four states of T cells: Th17, Treg, Th1, and Th2.

Macrophage M1 activity effects the induction of Th17 and Th1, while macrophage M2 activity effects the induction of Treg or Th2. Further, it has been found that the MRE complex ligand in accordance with the present invention is able to induce Th17 and Treg and to suppress the induction of Th1 and Th2.

IL-12p40 and IL-23p19, among a group of cytokines produced through a series of processes due to the stimulation of innate immune receptors, bind to intracellularly-residing p35 thereby turning into IL-12 and IL-23, respectively.

These four sets of cytokines control the T cells as below. (See FIG. 1)

In M1 Activity,
1) IL-12 causes differentiation of naive T cells (CD4) into Th1 and activation thereof.
2) IL-6 causes differentiation of naive T cells (CD4) into Th17; IL-23 and IL-1β activate Th17.

In M2 Activity,
3) IL-14 causes differentiation of naive T cells (CD4) into Th2 and activation thereof.
4) TGF-β causes differentiation of naive T cells (CD4) into Treg; IL-2 activates Treg.

The Th 1 and Th17 processes following the M1 activity provide antibacterial, antiviral, and anticancer and allergy suppressive actions; Th 2 following M2 activity leads to allergic reaction processes; and the Treg process provides inflammation suppression, tissue repair, and autoimmune suppression (immune tolerance) actions.

Herein, Th1 produces IFNγ by the action of IL-12. Activation of the phagocytosis and migratory ability of macrophages, natural killer cells, natural killer cells, and the like. Production of free radicals such as NO thereby enhances intracellular antibacterial potency. A process to eliminate intracellular parasitic bacteria and/or viruses is induced by an enhancement of the activity of CTL (killer T cell), CD8-T cells and an increase in cell-mediated immunity that kills cancer cells and virus-containing cells. This is primarily a non-antibody-dependent antibacterial and anti-viral process. It is also a process causing cytotoxic autoimmune cell diseases and/or delayed-type allergic diseases.

Th2 produces IL-4 and IL-13 and causes B cells to release IgE antibodies through mediation of CD4-T cells. IgE acts to eliminate large organisms such as parasites by secreting histamine from mast cells and/or basophils. In addition, it is also known to produce IL-5 thereby releasing EPO from eosinophils and induce delayed allergic conditions such as stuffy noses and the like.

Th17 has IL-1 and/or IL-23 operate to produce IL-17A, IL-17F, IL-22, IL-21, and the like. With an increase in humoral immunity, extracellular bacteria and fungi are eliminated by a vigorous production of antibodies. In addition, it increases neutrophilic phagocytosis, causes antimicrobial substances such as defensin to be released primarily from epithelial cells and neutrophils, and strengthens the epithelial barrier through an extracellular matrix remodeling. With a recent confirmed production of IL-21, a new process is being elucidated (See Non-patent Reference 3).

Treg, which characterizes intestinal immunity, is induced by TGF-β, producing IL-10, which is believed to be a process of inducing inflammation suppression and/or immune tolerance. Especially the intestinal tract with abundant enterobacteria is normally held in the Treg state so as to prevent lymphocyte immunity from running away, where its defense strength is delegated to the innate immunity of the epithelial cell lining and/or Paneth cells, and at the same time the enterobacteria are controlled by secretion of IgA, a secreting antibody, into the intestine through Peyer's patches. Treg is also known to suppresses inflammation by bringing into apoptosis, or suppressing, B cells that secrete allergy-causing Th1 and/or IgE and CTL (killer cells) that cause autoimmune diseases.

In regard to the MRE complex ligand, which follows the macrophage M1 activity process, as shown in the results of the previous Table, IL-23p19 and IL-12p40 increase; IL-4 does not change and TGF-βv rather tends to fall off, showing that the ligand activates Th17 and Th1 but not Th2 and Treg. In addition, the MRE complex ligand suppresses inflammation as in ulcerative colitis and Crohn's disease such that the process of the Trig being restored to normal with the MRE complex ligand in the actual intestinal tract is also believed to contribute to inflammation suppression and/or immune tolerance.

In order to sort out this finding, the drawn human blood was stimulated with the MRE complex ligand under controlled conditions thereby producing IL-23 the amount of which was determined as shown in Table 11.

TABLE 11

| IL-23 production test with human blood(pg/ml) | | | |
|---|---|---|---|
| Subject | Control | MRE complex ligand 6.00% dilution | Ratio relative to control |
| A male 72 | 46.9 | 92.8 | 1.98 |
| B Female 54 | 20.1 | 48.5 | 2.41 |
| C Male 31 | 21.3 | 40.0 | 1.92 |
| D Male 25 | 25.1 | 35.4 | 1.41 |
| Average | 28.4 | 54.4 | 1.92 |

The MRE complex ligand-containing solution increased IL-23 production to 1.92 times the normal level even on average; it was interesting to note that seemingly the older the subject the greater the IL-23 value. Accordingly, the MRE complex ligand increases the M1 activity of macrophages or the like, thereby activating Th17 and Th 1 and elevating cell-mediated immunity and humoral immunity so as to exert antibacterial, antiviral, and anticancer effects. This is consistent with clinical trials, including those shown in the Examples.

The Discovery of Novel Anti-Inflammatory Processes

An inconsistency has arisen between molecular physiology data and clinical observation in that while the MRE complex ligand very strongly activates the genes of inflammatory cytokines such as IL-1β, TNF-α, IL-8 and the like and activates Th-17 and Th1 processes, nevertheless for some reason, a beverage containing the MRE complex ligand significantly improves inflammation in cases of jaw inflammation, ulcerative colitis, atopic dermatitis, and the like.

To resolve this inconsistency, the inventors made intensive studies focused on the comprehensive DNA kinetic analysis of macrophages using a DNA array and the time sequential progress of cytokine production using human blood. As a result, it was determined that the MRE complex ligand expresses a novel immune process, not existing with the conventional ligands such as LPS. The first point is a suppressive action on IL-18 production by the MRE complex ligand. The current DNA kinetic analysis revealed, as shown in Table 12, that the MRE complex ligand suppresses the IL-18 production. This was a remarkable discovery.

TABLE 12

| Suppression of Inflammatory Cytokines | | |
|---|---|---|
| ILN18 | 0.55349 | IL-18 |
| CASP1 | 0.67590 | Caspase1 |
| Macrophage M1 activity | | |
| IL-23A | 1.78493 | IL-23p19 |
| IL-12B | 1.83736 | IL-12p40 |

IL-18 is a cytokine closely related to inflammatory diseases, which generates caspase 1 enzyme when stimulated by a conventional M1 ligand such as LPS; the caspase 1 cleaves an IL-18 precursor, producing IL-18. IL-18, then acts, in the presence of IL-12, on Th1 cells and/or NK cells, thereby strongly inducing IFN-γ production. This is because IL-12 increases IL-18 receptors in the Th1 cells and NK cells. Conversely IFN-γ, which Th1 cells produce, promotes the production of IL-12 and/or Il-18 from macrophages, in turn stimulating Th1 cells whereby a cycle will be formed to sustain and increase inflammation.

Thus, with a ligand such as LPS that commonly causes macrophage M1 activation, both IL-12 and IL-18 will rise.

However, the fact became clear that in the case of the MRE complex ligand, it suppresses IL-18 production while promoting the IL-1 and/or IL-23 production. As a fact to back this up, the level of CASP1 genes causing the expression of caspase-1 is 0.67590 times the normal level, as suppressed by the MRE complex ligand; and results have also been obtained confirming this by an IFN-γ production test using human blood. (See FIG. 5).

Now, known characteristics of IL-18 are that upon a simultaneous excessive production of IL-12 and/or IL-23 and IL-18, severe organ damage and autoimmune diseases develop in the intestines and the liver. In addition, conversely, in the co-presence of IL-12 and IL-18, the production of IL-4 and/or IL-13 is promoted where activation of a Th2 process leads to IGE production and histamine is released from the mast cells and/or basophils. Subsequently, upon IL5 production, EPO is released from eosinophils causing inflammatory conditions such as nasal congestion.

It has also been revealed that IL-18 by itself directly stimulates, with no IGE mediation, mast cells and/basophils thereby releasing histamine or inducing IL-4 and IL-13 production.

In particular, IL-13 is also known as a cytokine that induces bronchial asthma and/or pulmonary fibrosis (See Non-Patent Reference 4).

Furthermore, when Th1 cells are acted upon by IL-18 and TL-12 that originally activates Treg, the Th1 cells are transformed into cells called the super Th1, releasing IL-13, which is originally a Th2 cytokine, thereby causing bronchial asthma and lung fibrosis. It is believed that in the case of atopic dermatitis caused by *Staphylococcus aureus*, an aggravation also occurs by a similar mechanism. (Non-Patent Reference 6).

This is a remarkable fact. It is because IL-18 as a trigger is considered to switch Th1 cells, Th2 cells, Th17 cells, and the like between two states: inflammation and non-inflammation.

In a pro-inflammatory type activation process accompanied by an increase in IL-18, Th1 cells cause autoimmune diseases and Th2 cells cause allergic diseases. In an inflammation suppressive activation process accompanied by a decrease in IL-18, cell mediated immunities such as intracellular antibacterial activity, antiviral activity, and anticancer activity are reinforced.

In Th 2 cells, Il-4 and/or IL-13 and the like are produced in the co-presence of IL-18 thereby inducing allergic diseases. In case the level of IL-18 is low, a secretory immune process activates so as to secrete IgA from the intestinal tract and/or mammary gland.

Similarly in the case of Treg cells, the appearance of an IL-18 trigger results in a direct stimulation, with no IGE mediation, of the mast cells and/basophils thereby causing allergic diseases. It may be thought that also with Th 17, an IL-18 trigger causes a diversion into a process of promoting inflammation and that of suppressing inflammation.

For Th17, an increase in IL-18 induces IL-17A and/or IL-22, activating a humoral immune process. It is also known that an excessive production of IL-17 is highly inflammatory, developing autoimmune diseases such as chronic arthritis, multiple sclerosis, ulcerative colitis, Crohn's disease, and psoriasis. IL-22, closely associated with psoriasis, causes excessive production of HNP-3, an α-defensin.

Reduction in IL-18 causes induction of IL-17F and/or IL-2 whereby IL-17 activates a humoral immune process for elevating antibacterial and antiviral potency, such as vigorous antibody production and defensin secretion. In particular, IL-17 is known to promote the production of α-defensins, such as HNP1 to 2 and HNP4 to 6 from neutrophils as well as the production of β-defensins, hBD1 to 4, from epithelial cells (See Non-Patent Reference 7)

The second point of the notable action of the MRE complex ligand is its action to increase the IL-21.

The MRE complex ligand, by virtue of suppressing the production of inflammation-causing IL-18, is expected to effect the suppression of inflammations including allergies and/or autoimmune diseases, which actually is consistent with the clinical trial results for inflammatory diseases.

Further, as will be discussed below, it was confirmed that according to a cytokine test by drawing human blood, the IL-21 level with the MRE complex was also confirmed to nearly double the usual level (See FIG. 2). There was also a chance clinical confirmation that a non-Hodgkin's lymphoma patient (62 year-old female) taking the MRE complex ligand had a significantly elevated level of IL-21 in the blood. This patient's systemic metastatic cancer is on a decline, with the original lymphoma also confirmed to be on a shrinking trend.

IL-21 is a cytokine that elevates the anticancer activity by multiplying the secretion of antiviral agents and/or natural killer cells (See Patent References 4 and 5; Examples 8 to 13); separately, it also reportedly functions to cause apoptosis of T cells and B cells that cause autoimmune diseases (See Patent Reference 3).

It is known for IL-21 that there is a process wherein IL-12 is released from the macrophage M1 cells; and the IL-12 acts directly on NKT cells (natural and killer T cells), thereby inducing IL-21 production (See Patent Reference 2).

Figure 2:
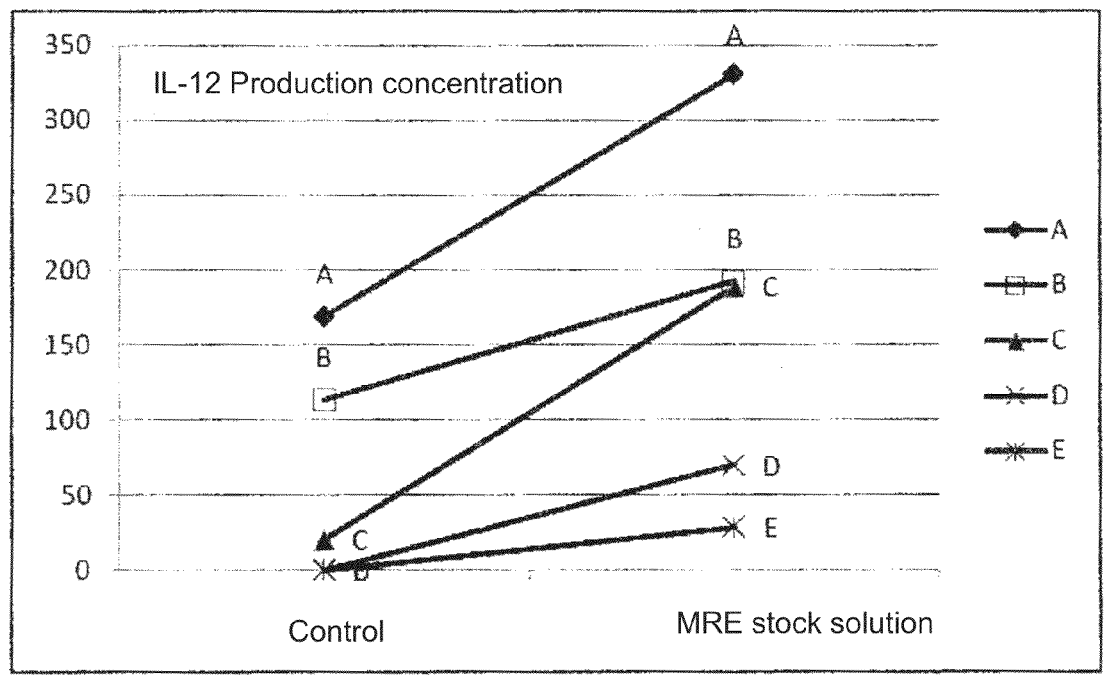
FIG. 2 is an IL-21 production trial graph using human blood. It compares IL-21 production concentrations among five subjects A to E with no stimulant (Control) IL and with the addition of a 6% dilute solution of the MRE beverage.
Figure 5:
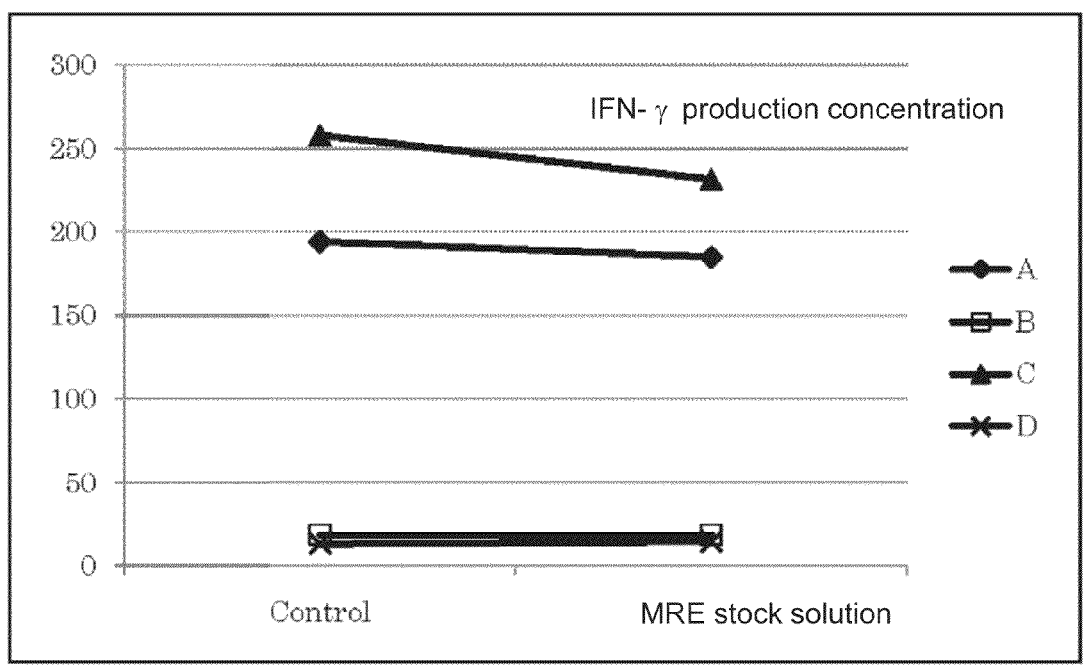
FIG. 5 is an IFN-γ production trial graph using human blood. It compares IFN-γ production concentrations among four subjects A to D with no stimulant (Control) and with the addition of a 6% dilute solution of the MRE beverage.

However, in the case of the MRE complex ligand, it has been confirmed that there are cases where with an increase in IL-23, Il-21 increases; moreover IL-21 increases even in the human blood in which neither IL-12 nor IFN-γ is produced such that it was inferred that a process with a route other than NKT cell activation from IL-12 is in operation (See FIGS. 2 and 5). Also, according to examples of the above Patent Reference 2, use is made of a high molecular weight simple ligand acting on TLR receptors such that said art was implied to be totally different in principle from the method of the present invention which makes use of a complex low molecular ligand for stimulating receptors three-dimensionally including intracellular innate immune receptors such as NLR.

That new principle has come to be elucidated in that Th17 activation induces the production of IL-21 from Th 17 (See Non-patent Reference 3) and furthermore that IL-21 has a cycle that promotes differentiation of Th17 cells and that secretes IL-21 on stimulation of IL-1 and/or IL-2 (Non-Patent Reference 8).

Thus the MRE complex ligand may be said to primarily produce IL-21 due to a Th17 non-inflammatory activation, and also secondarily to make use of an IL-121 production route due to an NKT cell activation via IL-12. Moreover, vertebrates, including humans, in fact, are constantly subjected to stimuli from ligands other than the MRE complex ligand such that these two IL-2 production routes would also constantly vary. In such cases the MRE complex ligand assumes characters more strongly as an adjuvant and will exhibit its excellent adjuvant effects.

In addition, the MRE complex ligand had 1.2 times the normal expression of cathepsin E genes that appear when the macrophages suppress inflammation.

Thus, the MRE complex ligand provides the amazing actions of calming inflammation while maintaining its activities toward the antibacterial, antiviral, and anticancer immunity processes. These facts have also been confirmed in the clinical trials to be described below.

Conventional pharmaceuticals for calming inflammation such as steroids and immunosuppressant drugs have had serious drawbacks in terms of reducing antibacterial potency. In addition, antibiotics were ineffective with viruses, have had the disadvantage of creating deadly resistant bacteria, and were also associated with side effects such as a breathing difficulty called anaphylaxis. The MRE complex ligands, which are free from these shortcomings, have turned out to be breakthrough immune activators as simultaneously effective antibacterial and anti-inflammatory agents.

In addition, the MRE complex ligand expresses FGF2, one of the cytokines that promote tissue repair, at 2.525 times the normal level and is capable of rapidly restoring tissue damage, which is also consistent with clinical trials.

The MRE complex ligand of the invention, as described above, performs a three-dimensional M1 activation of intra- and extra-cellular innate immune receptors including macrophages, microglia, dendritic cells, Langerhans cells, Kupffer cells, epithelial cells, keratinocytes, fibrotic cells, thereby causing the secretion of antibacterial and antiviral substances such as defensins and ISG as well as activating NK cells and NKT cells to cause apoptosis of cancer cells and virus-containing cells. It then activates NF-κB in two stages and secretes chemokines including IL-1β, TNF-α, and IL-8, producing at the same time multiple inflammation suppressors and/or mitochondrial SOD, thereby inhibiting cell damage due to TNF-α and the like. Further it causes the production of T lymphocyte cytokines, such as IL-6, IL-12, IL-12 and IL-23, differentiation of naive T cells into Th17 cells and Th1 cells, and activation of them. In addition the MRE complex ligand suppresses IL-18, a trigger of various diseases, and switches Th17 activity and Th1 activity for induction into non-inflammatory processes. This switching causes Th17 to produce IL-21 and IL-17. Further a cycle operates where the IL-21 differentiates naïve T cells into non-inflammatory IL-17. IL-17F enhances antibody production with activation of a humoral immune process free from inflammation, and in addition, secretes directly the innate immunity antibacterial substance defensins and/or antiviral substances, thereby exerting antibacterial and antiviral potency effects. Furthermore, the release of IL-12 causes IL-21 production from NKT cells without IFN-γ production. IL-21 in these cases exerts anticancer activity by directly increasing NK cell activities and in addition, causes apoptosis of autoimmune disease-causing T cells and/or B cells so as to suppress autoimmunity. Further, following through a process of induction from macrophage M1 activation to M2 activation for tissue repair; in progression are antibacterial, anticancer, antiviral, allergy suppression, anti-inflammatory, tissue repair, and autoimmunity suppression effects. In addition, macrophage activation invigorates phagocytosis thereof to facilitate the removal of wastes and foreign material in the blood, lymph, and tissue body fluid.

Utility as Adjuvant

In addition, the characteristics of the ligand of the present invention that suppresses inflammation enable its use as an excellent adjuvant equipped with properties of reducing the inflammatory side effects of various vaccines. The vaccines used in combination with the MRE complex ligand as an adjuvant, include antiviral and anti-bacterial vaccines such as vaccines for influenza, plague bacillus, and the like; new generation LPS, peptidoglycan, lipoarabinomannan, zymosan, lipopeptides, lipoteichoic acid, RSV-F protein, fibronectin EDA domain, HSP60, flagellin, unmethylated CpG DNA, double-stranded RNAs, polyinosinic polycytidylic acid, imidazoquinoline compounds, β-glucan, Maruyama Vaccine, *mycobacterium bovis*; and TLR ligands in OK-432 and the like, as well as vaccines containing bacterial cell components containing viruses bound thereto.

Blends with Mushroom- and Herb-Degradation Products

The MRE complex ligand can be used in blends with other immune ligands and/or immune adjuvants. In particular, it is highly compatible with carbohydrate chain type immune active ingredients in that degrading substances containing carbohydrate chain components such as lingzhi (reishi) mushroom, cordyceps, chaga mushroom (Inonotus obliquus), chitin chitosan, *Agaricus* and the like, to a level not more than a molecular weight of 8,000, followed by adding to the MRE complex ligand, exhibited a 49% to 60% increase in macrophage activity (viable cell count and NO production). This shows that the MRE complex ligand can function as an excellent adjuvant.

Combined use with substances containing ingredients inducing cancer [cells] to undergo apoptosis.

Cancer therapies with the combined use of a substance that restores apoptosis to cancer [cells] such as koto-sugi (family Taxaceae), resveratrol, quercetin or the like is also very effective.

Real Time PCR and DNA Microarray

Furthermore, the DNA kinetic analysis using a DNA microarray was carried out using the Human Gene 1.0 ST Array, Bio-Matrix Research.

Real-time PCR was carried out under the following conditions:

1. For cells used in the test solution, THP-1 cells (ECACC No88081201) derived from human peripheral blood monocytes, were incubated in an RPMI1640 medium supplemented with inactivated fetal calf serum, ampicillin sodium, and the antibiotic kanamycin sulfate, and used with the cell concentration adjusted to 2×E6 cells/ml.

2. For cell stimulation, 1.5 ml each of the cell suspension was placed in each well of a preliminarily prepared 6-well plate to be used as a test solution; negative and positive control wells were assigned; a stimulus sample was added to a positive control well, followed by shaking well, transferring to a 5% carbon dioxide gas incubator at 37° C., and culturing for 3 hours.

3. Extraction of total RNA was performed by extraction and conditioning according to the TRIzol protocol. DNA was cleaved for each sample by having a stroke fluid in and out for several times using a 1 ml syringe connected to 26 G needle, followed by conditioning and carrying out centrifugal separation at 4° C., 14000 rpm for 15 minutes thereby separating and extracting RNA.

4. The RNA was purified and evaluated for quality with agarose gel electrophoresis.

5. A DNAse I treatment was performed to remove the residual DNA from the purified RNA so as to synthesize cDNA.

6. For the synthesis of cDNA, it was synthesized using the Transcriptor First Strand cDNA Synthesis Kit, following the appropriate protocol.

7. Using the synthesized cDNA as a template, data were collected by running a real-time PCR.

For the DNA microarray, RNAs obtained by this procedure were used to analyze the comprehensive gene expression.

Thus, not only does the MRE complex ligand of the invention activate innate immunity and the subsequent lymphocytic acquired immune processes, but also it serves to suppress inflammation and enhance tissue repair potency. Accordingly, the MRE complex ligand of the invention has antibacterial, anticancer, antiviral, anti-inflammatory, tissue repair, and waste removal capabilities.

As mentioned earlier, it was revealed by a TNF-α production test with a real time PCR that the MRE complex ligand of the invention has a stimulation potency 7.54-fold that of LPS (endotoxin), which has powerful innate immune activation potency. It was also established that at the same time, numerous anti-inflammatory components appear and the mitochondrial SOD is produced such that TNF-α does not increase in the blood and no cell damage is caused. It was also confirmed that the MRE complex ligand has excellent specific properties in that it has no cytotoxicity in contrast to LPS. A fact was shown that on the one hand, with LPS, as its concentration increases, the viable cell counts of macrophages fall; on the other hand, as the MRE complex ligand concentration increases, viable cell counts of macrophages increase.

The MRE complex ligand of the invention, which is a low polarity, essentially electrical charge-free, oligo level low molecular ligand, is readily permeable through the cell wall so that it can stimulate and activate three-dimensionally and complexly not only the TLR receptors expressed on the cell surface but also NLR and/or RLR receptors expressed in intracellular endosomes and/or present in the cytoplasm. Such low molecular ligand can be readily absorbed through the intestinal wall, and can also be used, after purification thereof, for intravenous injections because they are not attacked by antibodies. This property provides synergistic effects with specific properties not seen with other ligands, along with the property of protecting cells and increasing cell viability with an increasing concentration thereof.

Now, the versatile and dynamic complex immune activation effects by the MRE complex ligand of the present invention having such specific properties will be explained below.

Macrophage Activity

Tables 13 and 14 show data where human macrophages were subjected to a diluted solution of the MRE complex ligand-containing stock solution prepared in "Example 1"; and the NO production and the viable cell count for the macrophage were determined.

TABLE 13

Human macrophage NO production test

| Test Samples | Concentration/dilution | Nitrite concentration($\mu$M) AV ± SD |
|---|---|---|
| Culture medium | 0 | −0.07 ± 0.46 |
| LPS (endotoxine) | 0.001 µg/ml | 10.02 ± 0.45 |
| LPS (endotoxine) | 0.1 µg/ml | 19.23 ± 0.56 |
| MRE complex ligand (Composition of the instant application) | 3,000-fold dilution | 3.64 ± 1.67 |
| MRE complex ligand (Composition of the instant application) | 300-folf dilution | 21.91 ± 2.23 |
| MRE complex ligand (Composition of the instant application) | 30-folf dilution | 22.72 ± 1.14 |

TABLE 14

Human macrophage activity test

| Test Samples | Concentration/dilution | Viable cell count index |
|---|---|---|
| LPS (endotoxine) | 0.001 µg/ml | 1.64 ± 0.02 |
| LPS (endotoxine) | 0.1 µg/ml | 1.47 ± 0.15 |
| MRE complex ligand (Composition of the instant application) | 3,000-fold dilution | 1.74 ± 0.10 |
| MRE complex ligand (Composition of the instant application) | 30-fold dilution | 2.47 ± 0.15 |

The results of determination show that the NO production with the MRE complex ligand-contaminating stock solution was greater than that with LPS; specifically the NO production with the 300-fold dilution thereof was as high as 2.19 fold. Despite the fact that the MRE complex ligand-containing stock solution gives an increase in NO, the macrophage viable cell count index increases with the MRE complex ligand-containing stock solution, which shows an opposite trend with the LPS in which the index fall off. Although not numerically shown herein, it is noted that there was no cell damage occurring even when the concentration of the MRE complex ligand-containing stock solution was increased up to an osmotic pressure limit. That is, the MRE complex ligand, causing no cell damage, is rather said to be an immune-activator with a macrophage activation effect, raising the viability of the macrophage.

Antimicrobial Effect

That the MRE complex ligand-containing stock solution is not directly bactericidal was established by a growth inhibition check test using *Escherichia coli, Pseudomonas aeruginosa, Staphylococcus aureus, Candida albicans*, and Black *aspergillus*. Therefore, the MRE complex ligand-containing stock solution contains no bactericides including antibiotics; and all the antibacterial effects seen in clinical trials can be ascribed to its immuno-competency.

Further, the antibacterial effects of the MRE complex ligand in accordance with the present invention can be summarized as follows: That is, the first point is its antibacterial effect due to an increase in macrophage phagocytosis; the second point is an antibacterial effect due to a release of antibacterial substances including defensins from macrophages, epithelial cells, keratinocytes, and the like. Specifically, it was confirmed that the release of PTX3, an antibacterial substance, from macrophages is 7.27-fold that of the normal level.

In addition, the third point is an antibacterial effect brought out by an increase in the phagocytic activity of neutrophils through Th17 activity, where phagocytosed bacteria are killed by HNP1 to 6, $\alpha$-defensins present in the azurophilic granules of the neutrophils. Since $\alpha$-defensins cause cell dysfunction such as a hemolyzing property, they are used exclusively inside the neutrophil.

Further, the fourth point is mentioned that the hBDs1 to 4, $\beta$-defensins, are secreted from epithelial cells and/or keratinocytes by the action of IL-17F, which is produced from Th17-17 cells. In addition, inflammatory IL-22 causes keratinocytes to secrete hBD3 therefrom to kill bacteria, but with psoriasis, IL-22 and the hBD3 are excessively secreted. The MRE complex ligand, which is ineffective for suppressing IL-22, is not capable of healing psoriasis, which is also consistent with clinical trials.

And the fifth point is that a CD4 humoral immune process is activated through a Th17 activation resulting in secretion of IgG from B cells and IgA from mucosal epithelial cells, thereby bringing on an antibacterial effects. It is IL-23 and IL-1 that activate the Th17; activation with a MRER complex ligand-containing stock solution caused IL-1b to express genes 47.64 times the normal, IL-4 6.3 times, and IL-23 1.78 times (a value still on the rise) the normal levels. The IL-23 production test using human blood has also confirmed an average secretion 1.92 times the normal level (See Table 11).

Antiviral Effect

The inactivation of the viruses in HIV and HCV diseases by the MRE complex ligand is noteworthy.

The anti-viral processes with the MRE complex ligand comprise the following.

The first one is the process by which TLR3, TLR7, TLR9, RIG1, and MAD5, innate immune receptors, are stimulated by the MRE complex ligand or the like, thereby directly secreting IFN and the like. Mainly released are IFN-$\alpha$ from macrophages, microglia and the like; IFN-$\beta$ from epithelial cells, fibroblasts, keratinocytes, osteoblasts and the like. These IFN-$\alpha$ and IFN-$\beta$ are sensed by the neighboring cells that have IFN receptors, resulting in a concurrent release of antiviral substances such as ISG or the like to exert antiviral effects.

The interferon gene expression in macrophages with the MRE complex ligand was as in Table 15.

TABLE 15

| Type I Interferon production (MΦ) | | |
|---|---|---|
| IL28a | 1.84637 | IFN-λ |
| ILNA6 | 1.67936 | IFN-α |
| IFN5 | 1.27655 | IFN-α |
| IFNB1 | 1.41305 | IFN-β |

The MRE complex ligand stimulation of the innate immune receptors has directly caused IFN-α5 to be expressed at 1.6 times the normal level, IFN-α6 1.2 times, and IFN-β 1.4-times. IFN-λ serves to enhance the ability to attack virus-infected cells with a NK-cell activating interferon.

This was also corroborated by the production of IFN-α in the drawn human blood as determined upon stimulation with the MRE complex ligand.

TABLE 16

| | Type I IFN-α production | | |
|---|---|---|---|
| Subject | Control | MRE complex ligand 6.00% dilution | Ratio to control |
| A female 51 | 1.0 | 4.2 | 4.2 |
| B female 54 | 4.1 | 21.1 | 5.1 |
| C male 72 | 7.8 | 14.3 | 1.8 |
| D male 25 | 4.7 | 11.2 | 2.4 |
| Average | 4.4 | 12.7 | 2.89 |

As shown in Table 16, it is seen that IFN-α is actually produced at an average of 2.89 times the normal level.

These are the values only for the ligand alone; if in fact there is a virus infection. the MRE complex ligand will act as an adjuvant, thereby further elevating the IFN-α value.

The second one is the production of type I IFN through IL-21. The MRE complex ligand is involved in activating the non-inflammatory Th17 process, producing IL-21. The IL-21 serves to activate the NK cells and also to promote production of type I IFN from epithelial cells, fibroblasts, keratinocytes, macrophages, and the like, whereby IFN-α and/or IFN-β cause antiviral substances to be released from still more cells.

The third one is that the MRE complex ligand produces IL-17F from Th17 and serves as an adjuvant to activate the humoral immune process, whereby in case there is a viral infection, it will play the role of enhancing antibody production against the viruses.

The fourth one is the clearance of virus-infected cells by the natural killer cells (NK), natural killer cells T (NKT), and cytotoxic T cells (CTL). As shown in Table 18, the MRE complex ligand activates natural killer cells. Furthermore, the MRE complex ligand, although not as a main function thereof, activates a Th12m process, thereby elevating cell-mediated immunity and also activating a process for clearing virus-infected cells and/or cancer cells.

The fifth one is that inactivation of viruses by oligopeptides has been found in the 1990s, so it cannot be dismissed that the MRE complex ligand, which is more than 90% made up of oligopeptides, may involve this process.

Thus, the MRE complex ligand has turned out to have excellent anti-viral effects by activation of the five processes.

In the present invention, the "virus" includes human immunodeficiency virus, hepatitis C, influenza virus, human papillomavirus (HPV), virus, human herpes virus, type B hepatitis virus, and DNA- and RNA-type viruses which infect fishes or higher vertebrates.

Anticancer Effect

Cancer cells undergo malignant transformation generally due to the compromised apoptosis of precancerous cells. Malignant transformation is always set off by the occurrence of a compromised apoptosis whether it is caused by an injury of cancer-suppressing genes with free radicals, by promoted degradation of p53 due to HPV as in cervical cancer, or by the compromised apoptosis with stress such as from HSP (heat shock protein) as in pancreatic cancer.

While there exist substances such as koto-sugi (family Taxaceae), quercetin, and resveratrol that restore the apoptotic function to immortalized cancer cells, the immune process exerts anticancer effects by having the cytotoxic CD8+ T cells (CTL) and NKT cells, and NK cells adhere to cancer cells and/or virus-infected cells, perforating the cells with perforin, and inducing cancer cells to apoptosis by granzymes.

On the other hand, TNF-α also activates a process that causes cytochrome C to be released from mitochondria and activates caspase-8 cells to induce cancer cells to apoptosis. However, TNF-α is known to be a substance which is highly cytotoxic to common cells and which can also trigger the onset of HIV.

In addition, in CTL, the cell-mediated immunity is reinforced by an IL-12 activated Th process activating CTL. However, the CTL destroys cells infected with type C hepatitis virus and/or HIV thereby causing the onset of hepatitis and/or HIV and also developing cytotoxic autoimmune diseases.

The anti-cancer effect of the MRE complex ligand is executed mainly by natural killer cells (cells NK) with the anticancer effect elevated with the participation of CTL cells and NKT cells.

NK cells are activated by the MRE complex ligand through the below processes to exert their anti-cancer effects.

The first one is a process in which stimuli of innate immune receptors cause type I interferon to be produced and directly activate NK cells, a process to show effects at an early period.

TABLE 17

| Cancer-relatedcytokines (MΦ) | | |
|---|---|---|
| IL-28A | 1.84637 | IFN-λ |
| CXCR4 | 0.67464 | Cancer metastasis |

With the MRE complex ligand, the gene expression of IFN-λ (IL-28A), known to strongly activates NK, is 1.84 times the normal level, as shown in Table 17, whereby it together with IFN-α and IFN-β elevates anticancer effects.

In addition, CXVR4 chemokine that causes cancer cells to metastasize to the lung and/or liver is suppressed to 0.67 times the normal level, thereby suppressing cancer metastasis.

The second one is the anti-cancer effects due to the activation of NK cells by producing Il-21 through a non-inflammatory Th 1 process with the MRE complex ligand.

The third one is a process of activating NK cells by a direct action from IL-12 on NKT cells, thereby producing IL-21.

The fourth one is the production of IFNγ by activation of the Th1 process with IL-12. It is a process for elevating the anticancer effect by activation of CTL. Thus, the MRE complex ligand is capable of activating NK cells by three processes.

Table 18 is for a comparison test for NK cell's ability to kill cancer cells. The comparison is made for addition of no ligand vs addition of the MRE complex ligand-containing stock solution prepared in Example 1.

TABLE 18

Test for ability to kill cancer cells by human NK cells.

| Subject | Control | MRE complex ligand (Composition of the instant application) | | | 6.00% Ratio to control |
|---|---|---|---|---|---|
| | | 0.06% | 0.60% | 6.00% | |
| A male 52 | 49.5 | 61.5 | 71.7 | 85.6 | 1.73 fold |
| B male 31 | 50.5 | 56.9 | 65.1 | 62.4 | 1.24 fold |
| C female 54 | 19.8 | 38.3 | 46.2 | 56.0 | 2.83 fold |
| D female 51 | 10.0 | 22.0 | 17.5 | 20.9 | 2.09 fold |
| Average | 32.4 | 47.6 | 51.6 | 56.2 | 1.73 fold |
| Rating | Standard | High | Very high | Very high | |

The method and procedure for testing NK cell's ability to kill cancer cells are given below.

The test used whole blood within 30 hours after collection. After separation of the PBMC by the Ficoll-Conray density gradient centrifugation method, the specimen was washed with RPMI (containing 10% FBS) to obtain Effector cells. This was incubated at $4.0 \times 10^6$ cells/ml PBMC for 24 hours under the four conditions shown below (5% $CO_2$, 37° C.).

Further, the applied MRE-complex ligand-containing stock solution concentration was set as a base level of 6.66% (v/v) concentration assuming a 100% absorption of the MRE fermentation stock into the blood, from an approximately 100 ml of a daily intake of the MRE-complex ligand-containing stock solution and a typical human blood volume of 4,500 ml.
(1) Control (=no addition).
(2) Addition of the MRE-complex ligand-containing stock solution (Concentration at incubation, 0.06% (v/v)).
(3) Addition of the MRE-complex ligand-containing stock solution (Concentration at incubation, 0.6% (v/v)).
(4) Addition of the MRE-complex ligand-containing stock solution (Concentration at incubation, 6.00% (v/v)).

After incubation, the Effector cells were mixed with labeled myeloid leukemia-derived K562 cells as Target cells and incubated for 4 hours (5% $CO_2$, 37° C.). In this case the Effector cells and target cells were mixed at a mixing ratio of E/T=40:1. After the incubation for 4 hours, the amount of $Eu^{3+}$ freed into each well was determined with a time-resolved fluorescence measurement, thereby permitting the calculation of the NK cells' cancer cell killing activity. The resultant numerical values represent what percentage of the NK cells killed K 562 cells, which are cancer cells.

Ratings for activity assessment designated: Very High for 51 or above; High for 42 to 51; Standard for 14b to 24; Very low for 14 or less.

Thus, the MRE complex ligand can activate NK cells by a variety of routes and can induce cancer to apoptosis at a Very High level.

Moreover, the apoptotic debris is rapidly phagocytized by macrophages without necrotizing as would with anticancer drugs and/or radiation so that the cancer is seen to shrink by itself without causing cachexia.

The MRE complex ligand offers good results in cases of a dog's liver cancer by intravenous injection (See Example 8); non-Hodgkin's lymphoma cancer by ingesting (See Example 13); and a renal cancer dialysis patient (See Example 39). These results are in close agreement with those of clinical results from IL-21 administration (Patent Reference 4). The precancerous polyps of viral cancer were also observed to disappear.

Further, the MRE a complex ligand, was found to have anticancer effects of reducing the cancer cells without concomitant inflammation.

Included in the term cancer herein are "abnormal cells" such as carcinoma, sarcoma, tumor, epithelioma, leukemia, lymphoma, polyp, rigid cancer, and, malignant transformation and neoplastic cells.

This is because NK cells are innate immune cells that select and eliminate only cells that deviate from "normalcy." (Non-patent reference 5).

Anti-Inflammatory Effect

The MRE complex ligand has excellent properties, not seen in any other ligands, in that while it maintains its anti-bacterial, antiviral, and anticancer effects, it has anti-inflammatory and tissue repair effects. The anti-inflammatory effect is also a remarkable nature of the MRE complex ligand.

In addition, the MRE complex ligand, in accordance with the present invention, suppresses inflammation by the following processes.

The first one reveals that it involves a pulse-wise progression of activation and a delayed suppression with a time lag so as to activate, in pulses, a coherent immune activation process, thereby holding a balance and homeostasis as an organism. Activation of NF-κB and AP-1 from the stimulation of TLR, NLR, and RLR is followed by maximization of ILIB (47.641), TNFA (21.182), and IL-8 (20.431) gene expressions, whereupon a NFKBIZ (20.011) gene expression, a "trigger" for the second stage of the process occurs vigorously and production begins the next phase products IL-6 (1.405), IL-12B (1.837), IL-23A (1.784), and the like. At the same time, the process proceeds with significant gene expressions of TNFAIP6 (37.142) and TNFAIP3 (18.830) that strongly suppress the first stage NF-κB; and expressions of NFKBIA (8.425) NFKBID (2.101), and IKBKE (1.447) genes that block and inactivate free NF-κB; followed by decreased expressions of NFKB1 (2.794 and NFKB2 (2.534), which are NF-κB genes (Numerals in parentheses are gene expression ratios relative to the normal level). The MRE complex ligand proceeds to suppress unnecessary inflammation. Chronic inflammation is believed to be a condition in which this suppression pathway becomes unworkable. Inflammatory diseases are seen to recover with the MRE complex ligand, presumably also due to the contribution of this process's normalization.

The second one is that the MRE complex ligand suppresses the production of IL-18, a trigger of inflammatory diseases. The reduced IL-18 production leads to the activation of a non-inflammatory Th17 process, non-inflammatory Th1 process, and non-inflammatory Th2 process.

The non-inflammatory Th17 process and non-inflammatory Th1 process are activated by the MRE complex ligand. IL-17 that activates non-inflammatory humoral immunity and IL-21 that activates NK cells are secreted from Th-17. IFN-γ is produced from Th1 to enhance cell-mediated immunity. While both processes retain antibacterial and antiviral potency, they act to calm inflammatory diseases including autoimmune and/or allergic diseases.

The third one is the calming of allergic diseases and autoimmune diseases by Il-21 production. The table below shows results for an IL-21 production test with human blood by the MRE complex ligand.

The method and procedure for NK cell's IL-21 production test are given as follows.

The test used whole blood within 30 hours after collection. After separation of the PBMC by the Ficoll-Conray density gradient centrifugation method, the specimen was washed with RPMI (containing 10% FBS) to obtain Effector cells. This was incubated at $4.0 \times 10^6$ cells/ml PBMC for 24 hours under the following conditions (5% $CO_2$, 37° C.). Further, the applied MRE-complex ligand-containing stock solution concentration was set as a base level of 6.66% (v/v) concentration assuming a 100% absorption of the MRE fermentation stock into the blood, from an approximately 100 ml of a daily intake of the MRE-complex ligand-containing stock solution and a typical human blood volume of 4,500 ml.

The effects on IL-21 production by the MRE-complex ligand-containing stock solution for the resultant PBMC were evaluated.

(A) Control (=no addition).
PBMC $1.0 \times 10^6$ cells/ml, PHAP-10 µg/ml; incubated for 24 hours (5% $CO_2$, 37° C.)

(B) Addition of the MRE-complex ligand-containing stock solution
PBMC $1.0 \times 10^6$ cells/ml, PHAP-10 µg/ml, MRE complex ligand-containing stock solution 6.00% (v/v); incubated for 24 hours (5% $CO_2$, 37° C.).

TABLE 19

IL-21 production test with human blood (pg/ml)

| Subject | Control | MRE complex ligand, 6.00% dilution | Ratio to Control |
|---|---|---|---|
| A male 72 | 169.3 | 331.0 | 1.96 |
| B male 31 | 113.0 | 192.2 | 1.70 |
| C female 54 | 20.5 | 188.5 | 9.20 |
| D female 51 | 0.0 | 69.7 | ∞ |
| E male 25 | 0.0 | 28.5 | ∞ |
| Average | 76.7 | 76.7 | 2.11 |

As shown in Table 19, the MRE complex ligand-containing solution is found to increase the IL-21 production on average to 2.11 times the normal level; it should be noted that subjects with only a low level IL-21 production to begin with tend to have a significant increase therein.

IL-21 is a cytokine that enhances anticancer effects by proliferating the anti-viral component secretion and natural killer cells and it is also known to induce allergy- and/or autoimmune disease-causing T cells and B cells to apoptosis.

The MRE complex ligand was confirmed to really increase IL-12 substantially in the human blood in this manner, which is also clearly corroborated by clinical trials for its effects, as in Examples 15 to 20.

In addition, also in the foregoing Table 4, the concentration of TNF-α, an inflammatory cytokine which is on average 232.8 ng/ml in the human blood when free of stimuli from ligand and the like slightly falls on average to 221.8 ng/ml even when stimulated with the MRE complex ligand. This result, when considered in comparison with the fact that a stimulus to macrophages alone with the MRE complex ligand at the same level gives a gene expression at 37.04 times the normal level (See FIG. 4) clearly demonstrates its anti-inflammatory effect.

Such IL-21 production-inducing effect by the MRE complex ligand is shown to be useful in preventing and treating a variety of immune diseases, such as allergic diseases (in particular, IgE regulated allergic diseases (Type I allergic reaction-related diseases) such as asthma, hay fever, atopic dermatitis, eczema, food hypersensitivity, urticaria, allergic rhinitis, allergic conjunctivitis, and the like; autoimmune diseases (rheumatoid arthritis, Crohn's disease, systemic lupus erythematosus, scleroderma, polymyositis, polychondritis, periarteritis nodosa, ankylosing spondylitis, rheumatic fever, Sjogren's syndrome, Behcet's disease, thyroiditis, diabetes type I, dermatomyositis, chronic active hepatitis, myasthenia gravis, Grave's disease, multiple sclerosis, primary biliary cirrhosis, autoimmune blood diseases (hemolytic anemia, hypoplastic anemia idiopathic thrombocytopenic thrombocytopenia, aplastic anemia, and the like), psoriasis, glomerulonephritis, lupus nephritis, Wegener's granulomatosis, sarcoidosis, Hashimoto's disease, Kawasaki disease, and collagen disease);
transplant rejection, inflammatory conditions (inflammation and pain in muscles and joints (rheumatoid arthritis, rheumatoid osteomyelitis, osteoarthritis, and uric acid arthritis), inflammatory skin conditions (eczema, and the like), inflammatory condition of the eyes (conjunctivitis and the like), disorders associated with inflammation of the lungs (asthma, bronchitis, and the like), digestive conditions associated with inflammation (aphthous ulcer, Crohn's disease, atrophic gastritis, verrucous gastritis, ulcerative colitis, celiac disease, focal ileitis, irritable bowel syndrome, and the like; gingivitis (inflammation after surgery or disorders, pain, and swelling), fever and pain associated with inflammation, inflammatory chronic kidney conditions (glomerulonephritis, lupus nephritis, membranous nephritis), uveitis, and contact dermatitis and the like), shock (septic shock, anaphylactic shock, adult-type respiratory distress syndromes and the like), cancer (lung cancer, stomach cancer, colon cancer, liver cancer, Hodgkin's disease and the like), and viral diseases (hepatitis and the like).

Tissue Repair Action

In general, the conversion of m1 macrophages (GM) to the M2 (M) M is believed to allow tissue repair by a process switching in action from an inflammatory antibacterial condition to inflammation suppression and tissue repair.

What brings about this conversion still remains unexplained. However, in reality, there is a first stage upon bacterial and/or viral invasion when bactericidal substances such as defensins and complement are released to kill bacteria, followed by englobing for processing by phagocytic cells of neutrophils, macrophages, and the like. With that defense net breached and neutrophils destroyed, lysosomal enzymes in the neutrophil are released, commencing inflammation. Inflammatory cytokines that warn of an emergency are secreted from dendritic cells, macrophages, and epithelial cells which sensed bacterial fragments. Further if the number of bacteria is large, immune cells are recruited followed by developing into an organized inflammation. At the inflammation site, the temperature is raised and the pH is shifted toward the acidic side thereby lowering bacterial and/or viral activities and at the same time creating an environment to facilitate the activities of emergency enzymes including the lysosomal enzymes. This is a process at an inflammation stage.

When the invading bacteria are completely destroyed, the fragments of destroyed bacteria are turned into low molecular substances by lysosomal enzymes and part thereof is sensed by the LHA receptors (MHC receptors in animals) of antigen presenting cells (APC) of macrophages, dendritic cells, vascular endothelial cells, with that information stored in memory T cells and memory B cells. Other parts thereof are sensed by LR, NLR, and RLR receptors of the macrophage innate immune system; the ligand pattern at the completion of antibacterial action is recognized, whereby the macrophages switch from the M1 to the M2 state releasing IL-10 and IL-2, and at the same time producing FGF that promotes tissue repair and activating fibroblasts, osteoblasts, and the like. At that occasion low molecular ligands are implied to signal the antibacterial completion pattern.

Since the MRE complex ligand is truly a product obtained by degrading bacterial cells down to low molecular products, it was possible to expect its tissue repair effects. The expression of FGF2, one of the cytokines that promote tissue repair was found to be 2.525 times the normal level by a DNA kinetic analysis with a microarray. The clinical trials also confirmed the MRE complex ligand's tissue repair action (See Examples 25 to 29).

Waste Product Removal

The macrophage M1 activation also activates macrophage phagocytic activity. This serves, in the blood, lymphocytes, and tissues, to phagocytize and degrade dead cells, foreign matter, and oxidized toxins such as oxidized LDL followed by discarding the residue in the bile for internal cleansing. The MRE complex ligand's M1 activation is effective for removing waste product through the activation of macrophages.

The MRE complex ligand has excellent properties for being simultaneously anti-inflammatory and antibacterial, antiviral, and anti-cancer. Said ligand, being low molecular in the oligo range, can be readily absorbed through the intestines and mucosa. In addition, it can also be utilized as a beverage and by topical application, or for intravenous injections after purification thereof.

The MRE complex ligand of the present invention can be said to possess, as its function, overall properties of suppressing lymphocytic immunity and enhancing innate immunity.

In addition, the immune-enhancing composition of the present invention exerts various innate immune stimulant effects as described above, on being administered to mammals, including humans, dogs and the like. Also, in these cases, the method of administration may be any mode of administration regularly performed in the medical or health care field as long as the immune-enhancing composition of the present invention is administered in such a state that its function can be exerted. For example, it can be administered enterally, orally, or may be done parenterally. Parenteral administration methods include intravascular administration, injection around or into the tissue, subcutaneous injection, and the like; it may also be applied directly to the skin and/or mucous membranes. Additionally permitted are intraocular administration, nasal administration, transdermal administration, and transmucosal administration.

In addition, the immune-enhancing composition according to the present invention can be administered in any formulation commonly used in the fields of medicine or healthcare or in the field of molecular biology, as long as such aspects permit exerting the functions of said composition. For example, the immune-enhancing composition according to the present invention can be administered as a liquid composition, wherein it may be a stock solution or a dilution.

Next, the efficacy of the present invention will be explained with the examples. However, the present invention is not intended to be limited to the examples described below, and it will be understood that various changes and modifications can be readily made by those skilled in the art.

Preparation of the MRE Complex Ligand

Example 1

Preparation of MRE Complex Ligand-Containing Stock Solution by Culturing and Internal Sporulation of an MRE Symbiotic Bacterial Group The MRE complex ligand-containing stock solution used in the present invention is prepared by degrading its own bacterial cells of the MRE symbiotic bacteria group down to a low molecular region by blended enzyme groups of the digestive enzyme group secreted from the vegetative cells of the MRE symbiotic bacterial group with a bulk-type enzyme group homologous to the lysosomal enzyme group released along with internal sporulation.

The culturing of the MRE bacteria group was carried out by a common culturing method known in the art for aerobic gram-positive bacteria. First, a 1.2 m$^3$ culture aeration vessel was filled with 1,000 l water and was aerated. The culture aeration vessel was fed with nutrients: 10 kg fish meal, 10 kg rice bran, 5 kg oil meal, 1 kg broth, along with appropriate amounts of minerals such as magnesium sulfate, silica, and the like. This was followed by adding the bacterial cells and incubating the MRE symbiotic bacterial group with aeration under culturing conditions of pH 6.0 to 6.8 and incubating temperatures of 25° C. to 35° C., with a continuous aeration so as to reach a dissolved oxygen concentration of 0.5 mg/L to 1.2 mg/L.

After the sufficient growth and stabilization of the bacteria has been attained, the MRE bacterial group in the vegetative cell state, along with the culture medium thereof, is separated into another aeration type culture vessel. In this culture aeration vessel, the system is placed under a starvation condition with all the MRE bacterial group's nutrients cut off, with continued aeration under the conditions of 25° C. to 35° C., whereupon the depletion of nitrogen components triggers an internal sporulation to begin. After awaiting till the transparency of the culture medium increases all at once, the aeration (oxygen feed) is stopped whereupon the internal spores all begin to precipitate, providing a transparent supernatant liquid.

Further, the resultant supernatant liquid is pressure filtered through a 0.2 μm membrane, to obtain a low molecular MRE complex ligand-containing stock solution. The MRE complex ligand-containing stock solution has 3.6 mg/ml of organic components, and contains therein 80 μg/ml of the MRE complex ligand component. It is noted in the present specification that the resultant "MRE complex ligand-containing stock solution" is called "The MRE stock solution"; the expression "dilution of the MRE complex ligand "refers to "dilution of the MRE complex ligand-containing stock solution" or "dilution of the MRE stock solution," unless specifically stated otherwise.

Clinical Trial Examples

Antiviral Effects

Example 2

AIDS (HIV)

Twenty persons, selected in an Asian farming village where more than half of its population of 800 are afflicted with HIV due to selling blood, were asked to ingest 200 ml per day of the beverage of the invention for one month. The ratio of CD4 positive T cells to the total T cells (CD4+/CD3) and the number of CD4 positive T cells per ml of the blood were determined for the three of those who took the beverage and for one who did not but used AIDS drug, by the flow cytometry method, providing results as shown in Table 20.

A year later all 20 persons who ingested the beverage were well and going about their daily lives including their work. No side effects have been reported at all.

TABLE 20

Efficacy of MRE complex ligand-containing stock solution for patients afflicted with AIDS

| Subject | Beverage of the invention used | (Number of CD4+cells)/ Total number of T cells | | Number of CD4 positive cells in the blood | |
|---|---|---|---|---|---|
| | | Before ingestion | 30 days later | Before ingestion | 30 days later |
| A female 32 | 200 ml/day | 12% | 20% | 90/ml | 145/ml |
| B female 34 | 200 ml/day | 18% | 29% | 120/ml | 297/ml |
| C female 54 | 120 ml/day | 26% | 32% | 255/ml | 348/ml |
| D female 51 | Not ingested | 5% | 2% | 29.4/ml | 23.0/ml |
| Standard values | | 29 to 55% | | 344 to 1289/ml | |

Example 3

Hepatitis C Virus (HCV)

A male, 48 years of age with hepatitis C virus, who had been treated with interferon and ribavirin, had a viral load of 28,000/ml, ALT(GPT) of 621, AST(GOT) of 586, which had not dropped significantly, began ingesting the MRE beverage. He took 50 ml per day in addition to Urso. Three months later, the viral load determined with PCR dropped to 12,800/ml. With the ALT (GPT) dropped to 48 and AST (GOT) to 52, a considerable improvement was made.

Example 4

Cervical Cancer (HPV)

A female, 50 years of age. Ingestion of 30 ml of the MRE mix ligand beverage, twice a day (mornings and evenings). A test two months later showed an improvement from Class 3a to 2a.

Example 5

A Predisposition to Catch Colds Frequently

A girl, 6 years of age. Was frail and caught cold frequently. Often had lasting high fevers of 38.5° C. or higher. Three months after she started continuous ingestion of 20 ml of the MRE beverage twice a day, she has stopped getting colds.

Example 6

Warts/(HPV)

A male, 71 years of age. Had warts on the fingers interfering with his work. After he continued ingesting the MRE beverage, 50 ml a day for 6 months, the warts have shrunk to a level no longer noticeable. Warts are said to be caused by HPV (human papillomavirus).

Example 7

Zoster

A female, 60 years of age. Ingested 30 ml of the MRE beverage twice daily along with a topical application thereof to the affected site. An improvement was seen in 1 to 2 days. The herpes and/or zoster heals faster with topical application simultaneous with the ingestion.

Antibacterial Effect

Example 8

Chronic Infection

A female, 58 years of age. Had fatigue due to systemic bacterial infections (opportunistic infections) resulting in swelling and inflammation of the instep, ankle, malleolus, thumb, and like sites, which varied at every occurrence. The rheumatoid factor was negative, and she had a repeated cycle of healing by taking antibiotics. Then antibiotics lost their efficacy, prompting her to take the MRE beverage, 50 ml twice a day, on a trial basis. As a result, what used to be 1 to 3 onsets of affliction per month is now about one episode per six months. The elevated platelet count also began to decline.

Example 9

Bedsores

A female, 80 years of age. Bedsores-turned infection. The MRE beverage was sprayed onto the bedsore site and gauze was soaked in it to be compressed to the site. The suppuration began to diminish; the bedsores became smaller a month later, and the odor emanating from the wound site also declined.

Anticancer Effect

Example 10

Liver Cancer

An old male dog, 12 years of age. Liver cancer made it unable to take either water or feed, and was left lying down and immobile. With no way to treat it, it was injected with the MRE beverage on a trial basis. On the third day, it got up and started drinking water, so it was administered with water mixed in with 100 ml of the MRE beverage; whereupon it began eating the feed and went on to get well. The veterinarian at an animal hospital was quoted as saying that the cancer appeared to have shrunk and it was completely cured.

Example 11

Liver Cancer

An old male mongrel dog, 13 years of age. It received the diagnosis at Yamaguchi University, Department of Veterinary Medicine that "the dog has numerous malignant tumors in the liver and there is no way to treat it whatsoever." Since the dog was in a condition that did not permit surgery, it was administered with a water-diluted MRE beverage every day. A week later, it was re-examined at the University and received the diagnosis that the cancer did not grow. Thereafter the dog willingly started drinking the MRE beverage and recovered day by day; a month later it started running around in the house. An X-ray examination 3 month later revealed that the cancer shrunk to a small size. The routines of going out and taking meals were restored, and it was well and jumping around.

Example 12

Liver Cancer

A female, 75 years of age. Simultaneous onset of liver cancer and diabetes; used insulin injections. Had 50 ml of the MRE beverage twice a day. In about two months, cancer cells shrank and the glucose levels prior to insulin injection have declined.

Example 13

Improved Liver Function

A male, 42 years of age. Liver function test gave an ALT (GPT) value of 64. Ingested 30 ml of the MRE beverage twice a day. A test one month later gave an ALT value of 58; and a test 2 month later an ALT value of 33, a normal level.

Example 14

Prostate Cancer

A male, 61 years of age. End-stage prostate cancer with the blood PSA value exceeding 3,000/ml. On the verge of bone metastases; the vomiting of blood from the mouth. Inoperable; received subcutaneous injection of Casodex, an anti-androgen, and that of Leuplin, a female hormone once per 4 weeks. The PSA value temporarily dropped to 1 only to relapse. Then, the Casodex was replaced with more effective Odyne. However, there is a risk of Odyne causing serious liver damage. Blood test showed PSA to be 0.92, but AST (GOT) rose to 56 (a normal level: 11 to 30) and ALT (GPT) to 196 (a normal level: 4 to 30)). Since continuation of this condition meant a shift to the use of an anticancer agent with the accompanying pain, the patient continued to ingest 250 ml of the MRE beverage every day. As a result, the PSA, AST, and ALT values were all held at normal levels, to the point where the patient was well enough to be able to have beer and cigarettes and enjoy playing tennis once or twice a week.

Example 15

Stomach Cancer

A male, 70 years of age. Tumors grew large with metastasis of liver cancer to the stomach. Became unable to take meals. Ingested 30 ml of the MFRE beverage twice a day, along with an intravenous infusion treatment. In a month or two, the stomach and liver tumors began to shrink; 4 months later, the patient became able to take meals. According to a test 5 month later, the tumors appeared to be all but eliminated.

Example 16

Colorectal Cancer

A male, 69 years of age. Hospitalized with colon cancer. Ingested 80 ml of the MRE ligand beverage a day. Thereafter, the tumor markers began to fall off; a month later the tumors themselves became smaller. A resection operation was performed; there were no lymphatic metastases.

Example 17

Pancreatic Cancer

A male 66 years of age. Was under an anticancer treatment for pancreatic cancer. Also received insulin injections for diabetes. Ingested 30 ml of the MRE ligand beverage a day for several months; the patient is in a very good physical condition.

Example 18

Rectal Cancer

A female, 78 years of age. Has a colostoma. Declared incurable as told by the physician to her family. Ingested 2 bottles (1800 ml) of the MRE ligand beverage on day 1; one bottle (900 ml) on day 2; and one bottle (900 ml) on day 3. A subsequent test showed eliminations including the metastasized cancer to the bone.

Example

Lung Cancer

A male, 76 years of age. Took anticancer agent TS-1 for lung cancer metastasized to the bone. Though the initial efficacy was good enough to hold hope for recovery, it waned. Treatments for severe pain and constipation at hospice with narcotics and laxatives. The patient then ingested 30 ml of the MRE ligand beverage three times a day. An examination 3 weeks later showed the disappearance of the lung cancer (although it remained in the bone). The patient was able to return to work.

Example 20

Malignant Lymphoma

A female, 62 years of age. Stage 4 non-Hodgkin's lymphoma with metastasis throughout the body, forming a rubber ball-like tumor at the jaw portion below the ear. Under a physician's supervision, with no treatment with medicines such as anticancer agents, the patient received an intravenous infusion of a large dose of vitamin C; and also ingested 50 ml of the MRE beverage twice a day. Three months later the level of IL-21 in the blood considerably increased; the metastasized cancer began shrinking and the tumor at the jaw portion below the ear became soft.

Anti-Inflammatory Effect

Example 21

Temporomandibular Arthrosis

A male, 64 years of age. A temporomandibular joint inflammation in the right side kept his mouth unopenable. Had dental treatment for tooth decay, but that did not bring about his recovery at all. Began ingesting 100 ml of the MRE beverage a day. The following day the fever of the jaw receded and pain lessened; 3 days later, it was possible to open his mouth; he recovered enough to take meals as usual. He recovered back to normal about a week later.

Example 22

Urticaria

A female, 31 years of age. Nearly daily development of systemic urticarial rash of unknown cause. Had 50 ml of the MRE beverage ingested. Became less itchy and more bearable in about one hour after the ingestion. With another rash development next day, it was decided to have her ingest the beverage twice a day. After about one month passed, urticarial rash no longer developed.

Example 23

Urticaria

A female, 54 years of age. Hives, the size of a 500 yen coin, shrank to a little finger size 2 days after the ingestion; what took a week for the hives to subside now subside in 2 to 3 days with the skin becoming smooth.

Example 24

Ulcerative Colitis

A female, 49 years of age. Ulcerative colitis has periodically kept her in and out of a hospital. A steroid drug was used for a simultaneous eruption of a rather severe urticarial-like drug rash due to side effects from Pentasa and Salazopirin. The drug rash stopped about one month after a daily ingestion of 200 ml of the MRE beverage of the present invention started. Subsequently hospital visits and medication were discontinued. Later, endoscopy showed no finding of inflammation about 10 months after she started ingesting the MRE beverage. Then diet therapy and ingestion of the MRE beverage continued. No more symptoms of ulcerative colitis with no medication other than a drug for controlling intestinal function.

Example 25

Atopic Dermatitis

A female, 31 years of age. Suffered from atopic-like inflammation with the skin swelling and itching throughout the entire body including the face. Spraying the MRE beverage like a lotion was found to temporally reduce swelling and itching substantially. Ingestion of 30 ml of the MRE beverage twice a day made it less likely for a rash to erupt.

Example 26

Hornet

A male, 65 years of age. Immediately after being stung by hornets, the MRE beverage was applied to the head, leading to a recovery with no swelling.

Example 27

Centipede

A male, 28 years of age. Four months after having been bitten on the foot by a centipede, a swelling failed to subside, with bite marks remaining just like an elastic sock stretch mark. Ingestion of 30 ml of the MRE beverage once a day resulted in having the swelling subside beginning on the $10^{th}$ day. The patient is in a state where swell develops when the ingestion is forgotten; then the ingestion brings the swell down.

Example 28

Allergic Rhinitis

A female, 16 years of age. Allergic rhinitis. Ingestion of 30 ml of the MRE beverage twice a day. The symptoms improved in three weeks.

Diabetes and Hypertension

Example 29

Diabetes

A male, 56 years of age. Had diabetes with a varied range of fasting blood glucose levels and the A1C value exceeding 8.6. One month after starting to ingest 180 ml of the MRE beverage a day, his fasting blood glucose level dropped to 134 and the A1C value to 7.6. The fasting blood glucose level of 90 and A1C of 7.3 in 2 months; the fasting blood glucose level of 89 and A1C of 5.8 in 3 months; the fasting blood glucose level of 91 and A1C of 5.0, normal levels, in 4 months.

Example 30

Diabetes

A male, 70 years of age. Father and older brother died of diabetes. The subject's condition deteriorated to the point where insulin injection would be required. After a continued ingestion of the MRE beverage, his diabetes was said to have gotten better according to his physician, when he was allowed to stop taking medication. Since then he has never been told that he had a high glucose level in the blood and claims he is fine drinking rice wine every day.

Example 31

Hypertension

A male, 70 years of age. Had a systolic blood pressure of 160 and a diastolic blood pressure of 98, which dropped to 140 s and 80 s after the ingestion of 30 ml of the MRE beverage twice a day for one month.

Example 32

Hypertension

A male, 72 years of age. Blood pressure, 160/90. Ingestion of 50 ml of the MRE beverage twice a day brought the blood pressure to 130/80. An about 3 cm size blotch he had also became smaller.

Tissue Repair Effects (Recovery from Bone Fracture and Wounds)

Example 33

Post Surgery Scar

A male, 61 years of age. Had abdominal surgery and was told to take at least 6 months before the suture was removed because of his diabetes. Ingestion of 50 ml of the MRE beverage once a day allowed the suture to be removed in one week.

Example 34

Ligament Damage

A male, 42 years of age. Had ligament damage in his left knee, which was diagnosed as "will be possible to walk but difficult to run" even with rehabilitation thereof. His conditions had not been improved even after 5 years, with pain in the left leg remaining on running or overstraining himself.

Two weeks after starting an ingestion of the MRE beverage, it was noticed that there was no more left leg's pain even after a bicycle ride. Was able to run though for only 5 m. Continued ingestion of the MRE beverage allowed extending the running distance to 10 m and 20 m. Once when he stopped ingestion for a week, a pain was felt during a long bicycle ride and a discomfort felt on running, too. The patient is putting in an effort to extend the running distance, aimed at a 5 km marathon run.

Example 35

Bone Fractures

A female, 88 years of age. Suffered a bone fracture and was told by the physician that it would take half a year for the bones to join together. With the ingestion of the MRE beverage the bones joined in one month.

Example 36

Low-Temperature Burns of the Foot

A female, 73 years of age. Had treatment for severe low temperature burns of the foot for a month, which resulted in no granulation. Granulation began after a week's ingestion of 30 ml of the MFRE beverage twice a day.

Example 37

Acne Scars

A female, 61 years of age. Had contoured "acne scars" on the nose when the "acne" was squeezed when she was a high school student. Ingested 50 ml of the MRE beverage a day. At about $2^{nd}$ month thereof, the acne scars began to shrink; in 6 months the scars shrank considerably although not completely; the skin unevenness began to be not noticeable. Overall skin texture also turned smooth.

Example 38

Postoperative Floaters

A male, 51 years of age. Had floaters after retinal detachment surgery. Ingestion of 50 ml of the MRE beverage saw an improvement in 2 weeks; in addition, the blood pressure which used to be 150 or higher has no longer exceeded 130.

Example 39

Improved Kidney Function

A male, 51 years of age. A renal dialysis patient.

TABLE 21

| BUN value | At ingestion startup | First month | Third month |
|---|---|---|---|
| Before dialysis | 68.8 mg/dl | 68.1 mg/dl | 51.5 mg/dl |
| After dialysis | 68.8 mg/dl | 21.9 mg/dl | 17.7 mg/dl |
| Normal range: 8 to 20 mg/dl | | Life-threatening value: 80 mg/dl | |

As shown in Table 21, the BUN values which had not changed much before ingestion of the MRE beverage had begun to drop gradually with the start of the ingestion, though still within control levels. Above all, the patient was happy regaining stamina. Note that the after-dialysis value at the third month since the ingestion of the MRE beverage began turned out to be a normal one.

Although detailed data are not available, there are two other renal dialysis patients who have been ingesting the MRE beverage. One has come to urinate a little on his own. Both of the two have recovered and returned to farm work or to the workplace.

Test Ingestion Cases by Healthy Subjects

Example 40

Ingestion Tests by Healthy Subjects

A survey was conducted on 72 healthy people who sampled the MRE beverage. 58 out of the 72 reported an improved urine flow; 41 of the 72 felt they no caught a cold; 68 of the 72 now have a lustrous skin. No likely side effects were noted by those including those who become constipated with herbs. 12 rather claimed improvements in constipation.

In addition, the present invention can be modified in various ways, though needless to mention, with the various modification being not limited to the embodiment described above, within the scope of not changing the gist of the invention.

What is claimed is:

1. An immune enhancing composition that enhances a subjects innate immunity by stimulating the innate immunity thereof, comprising: an immunostimulant, as an effective ingredient, generated by degrading bacterial cells of a Mitarai Enzyme (MRE) symbiotic bacterial group comprising *Bacillus* sp. FERM BP-11209, *Lysinibacillus fusiformis* FERM BP-11206, *Bacillus sonorensis*, *Lysinibacillus* sp. FERM BP-11207, and *Comamonas* sp. FERM BP-11208, wherein said immunostimulant is obtained by incubating the bacterial cells of said MRE symbiotic bacterial group, under a culture condition suitable for growth, placing a resultant culture medium under a starvation condition, thereby causing the bacterial cells of said MRE symbiotic bacterial group to internally sporulate, and by removing from said culture medium impurities containing said internally sporulated bacterial cells of said MRE symbiotic bacterial group.

2. The immune-enhancing composition as set forth in claim 1, wherein
said immunostimulant is composed at least 98% by weight thereof or more of a hydrophilic low molecular substance of an average molecular weight of not more than 1,000 Da.

3. The immune-enhancing composition as set forth in claim 1, wherein said immunostimulant activates macrophages, natural killer cells, or natural killer T cells.

4. The immune-enhancing composition as set forth in claim 1, wherein
said immunostimulant activates dendritic cells, microglial cells, Langerhans cells, or Kupffer cells.

5. The immune-enhancing composition as set forth in claim 1, wherein
said immunostimulant activates epithelial cells, fibroblasts, keratinocytes, or osteoblasts.

6. The immune-enhancing composition as set forth in claim 1, wherein
said immunostimulant causes differentiation or activation of Th1 or Th17.

7. The immune-enhancing composition as set forth in claim 1, wherein
said immunostimulant enhances IL-21 production.

8. The immune-enhancing composition as set forth in claim 1, wherein
said immune-enhancing composition is used as an anti-inflammatory agent in a subject afflicted with an allergic or autoimmune disease.

9. The immune-enhancing composition as set forth in claim 8, wherein
said allergic or autoimmune diseases are selected from a group consisting of temporomandibular arthrosis, ulcerative colitis, atopic dermatitis, and allergic rhinitis.

10. The immune-enhancing composition as set forth in claim 1, wherein
said immune-enhancing composition is used as an adjuvant for vaccines against pathogenic bacteria or pathogenic viruses.

11. The immune-enhancing composition as set forth in claim 10, wherein
said pathogenic bacteria or pathogenic viruses are selected from a group consisting of opportunistic infectious bacteria, HIV, HCV, and HPV.

12. The immune-enhancing composition as set forth in claim 1, wherein
said immune-enhancing composition is used as food or feed.

13. A method for preparing an immune enhancing composition that enhances a subjects innate immunity by stimulating innate immunity thereof, comprising: preparing and incubating bacterial cells of a Mitarai Enzyme (MRE) symbiotic bacterial group comprising *Bacillus* sp. FERM BP-11209, *Lysinibacillus fusiformis* FERM BP-11206, *Bacillus sonorensis*, *Lysinibacillus* sp. FERM BP-11207, and *Comamonas* sp. FERM BP-11208;
degrading the bacterial cells of said prepared MRE symbiotic bacterial group; and removing impurities from a culture medium in which the bacterial cells of said MRE symbiotic bacterial group were incubated; wherein said degrading step is carried out by incubating the bacterial cells of said prepared MRE symbiotic bacterial group under a culture condition suitable for growth and placing a resultant culture medium under a starvation condition, thereby causing the bacterial cells of said MRE symbiotic bacterial group to be internally sporulated.

* * * * *